(12) United States Patent
Jones et al.

(10) Patent No.: US 7,259,254 B2
(45) Date of Patent: Aug. 21, 2007

(54) MUTANTS AND ASSAY SYSTEM TO IDENTIFY USP/RXR LIGANDS

(75) Inventors: Grace Jones, Lexington, KY (US); Davy Jones, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 397 days.

(21) Appl. No.: 10/719,024

(22) Filed: Nov. 24, 2003

(65) Prior Publication Data

US 2005/0054569 A1 Mar. 10, 2005

Related U.S. Application Data

(60) Provisional application No. 60/428,282, filed on Nov. 22, 2002.

(51) Int. Cl.
*C07H 21/02* (2006.01)
*C07H 21/04* (2006.01)
*C07K 1/00* (2006.01)

(52) U.S. Cl. .................... 536/23.1; 536/23.5; 530/350; 530/858

(58) Field of Classification Search ...................... None
See application file for complete search history.

(56) References Cited

FOREIGN PATENT DOCUMENTS

WO          WO 01/71042 A2 * 9/2001

OTHER PUBLICATIONS

Oro et al. 1990. Nature 347:298-301.*
G. Jones, et al. "Juvenile hormone III-dependent conformational changes of the nuclear receptor ultraspiracle" Insect Biochemistry and Molecular Biology 32 (2001), pp. 33-49.
G. Jones, et al. "Ultraspiracle: An Invertebrate nuclear receptor for juvenile hormones" Biochemistry, Proc. Natl. Acad. Sci. USA, vol. 94, pp. 13499-13503, Dec. 1997.
M. Harmon, et al. "Activation of mammalian retinoid X receptors by the insect growth regulator methoprene" Biochemistry, Proc. Natl. Acad. Sci. USA, vol. 92, pp. 6157-6160, Jun. 1995.
Y. Xu, et al. "Activation of transcription through the ligand-binding pocket of the orphan nuclear receptor ultraspiracle" Eur. J. Biochem., 269, pp. 6026-6036 (2002), FEBS.
M. Lezzi, et al. "The Ecdysone Receptor Puzzle" Archives of Insect Biochemistry and Physiology 41: 99-106, Wiley-Liss, Inc. 1999.
H. T. Tran, et al. "Requirement of co-factors for the ligand-mediated activity of the insect ecdysteroid receptor in yeast" Journal of Molecular Endocrinology (2001) 27, pp. 191-209, Society for Endocrinology.
T. Dhadialla, et al. "New Insecticides with Ecdysteroidal and Juvenile Hormone Activity" Annual Review of Entomology, 1998, 43: pp. 545-569.
Egea, et al. "Crystal structure of the human RXRα ligand-binding domain bound to its natural ligand: 9-*cis* retinoic acid" The EMBO Journal, vol. 19, No. 11, Jun. 1, 2000, pp. 2592-2601.

G. Jones, et al. "Considerations on the structural evidence of a ligand-binding function of ultraspiracle, an insect homolog of vertebrate RXR" Insect Biochemistry and Molecular Biology 30 (2000), pp. 671-679.
I. Billas, et al. "Crystal Structure of the Ligand-binding Domain of the ultraspiracle Protein USP, the Ortholog of Retinoid X Receptors in Insects" The Journal of Biological Chemistry, vol. 276, No. 10, Issue of Mar. 9, pp. 7465-7474, 2001.
G. Clayton, et al. "The structure of the ultraspiracle ligand-binding domain reveals a nuclear receptor locked in an inactive conformation" PNAS, Feb. 13, 2001, vol. 98, No. 4, pp. 1549-1554.
Bogan, et al. "Natural ligands of nuclear receptors have conserved volumes" nature structural biology, vol. 5, No. 8, Aug. 1998, pp. 679-681.
R. Notle, et al. "Ligand binding and co-activator assembly of the peroxisome proliferators-activated receptor-μ" Nature, vol. 395, Sep. 10, 1998, pp. 137-143.
S. Kliewer, et al. "A Prostaglandin $J_z$ Metabolite Binds Peroxisome Proliferator-Activated Receptor μ and Promotes Adipocyte Differentiation" Cell, vol. 83, Dec. 1, 1995, pp. 813-819.
A. Brzozowski, et al. "Molecular basis of agonism and antagonism in the oestrogen receptor" Nature, vol. 389, Oct. 16, 1997, pp. 753-758.
A. Shiau, et al. "The Structural Basis of Estrogen Receptor/Coactivator Recognition and the Antagonism of This Interaction by Tamoxifen" Cell, vol. 95, Dec. 23, 1998, pp. 927-937.
R. Watkins, et al. "The Human Nuclear Xenobiotic Receptor PXR: Structural Determinants of Directed Promiscuity" Science, vol. 292, Jun. 22, 2001, pp. 2329-2333.
G. Jones, et al. "Identification of regulatory sequences of juvenile hormone-sensitive and -insensitive serum protein-encoding genes" Gene, 173, pp. 209-214, 1996.
G. Jones, et al. "Transcription of the juvenile hormone estarase gene under the control of both an initiator and AT-rich motif" Biochem. J. (1998) vol. 335 part 1, pp. 79-84.
G. Jones, et al. "Regulation of the juvenile hormone esterase gene by a composite core promoter" Biochemical Journal, vol. 346, Part 1, Feb. 15, 2000, pp. 233-240.
D'Avino, et al. "The moulting hormone ecdysone is able to recognize target elements composed of direct repeats" Molecular and Cellular Endocrinology, vol. 113, No. 1, Aug. 30, 1995, pp. 1-9.

(Continued)

*Primary Examiner*—Lorraine Spector
*Assistant Examiner*—Shulamith H. Shafer
(74) *Attorney, Agent, or Firm*—McDermott Will & Emery LLP

(57) ABSTRACT

The invention relates to mutant nuclear hormone receptors that encode mutant nuclear hormone receptors, in which particular amino acid residues are substituted with respect to wild type, so as to be able to detect ligand binding to the mutant receptor by either a change in a physical property of the mutant receptor and/or an transcriptional induction of a nuclear hormone receptor construct. The invention also relates to a nuclear hormone receptor response element denoted by the formula YDRXZ comprising a direct repeat (DR) comprising two half sites separated by X nucleic acid bases; wherein Z indicates the presence of at least one DR oriented in either a forward or reverse orientation; wherein Y equals 1 to 8 forward and/or reverse direct repeats; and X equals 1 to about 12.

20 Claims, 7 Drawing Sheets

OTHER PUBLICATIONS

A. Steinmetz, et al. "Binding of Ligands and Activation of Transcription by Nuclear Receptors" Annual Review of Biophysics and Biomolecular Structure, vol. 30, 2001, pp. 329-359.

S. Kersten, et al. "On the Role of Ligand in Retinoid Signaling: Positive Cooperativity In the Interactions of 9-*cis* Retinoic Acid with Tetramers of the Retinoid X Receptor" Biochemistry 1995, vol. 34, pp. 14263-14269.

S. Strugnell, et al. "Bacterial Expression and Characterization of the Ligand-Binding Domain of the Vitamin D Receptor" Archives of Biochemistry and Biophysics, vol. 364, Issue 1, pp. 42-52, 1999.

J. Lupisella, et al. "The Ligand Binding Domain of the Human Retinoic Acid Receptor μ is Predominantly α-Helical with a Trp Residue in the Ligand Binding Site" The Journal of Biological Chemistry, vol. 270, No. 42, Oct. 20, 1995, pp. 24884-24890.

J. Reid, et al. "Conformational Analysis of the Androgen Receptor Amino-terminal Domain Involved in the Transactivation" The Journal of Biological Chemistry, vol. 277, No. 22, May 31, 2002, pp. 20079-20086.

M. Schimerlik, et al. "Kinetic and Thermodynamic Analysis of 9-*cis*-Retinoic Acid Binding to Retinoid X Receptor α" Biochemistry, vol. 36, Issue 21, May 1999, pp. 6732-6740.

* cited by examiner

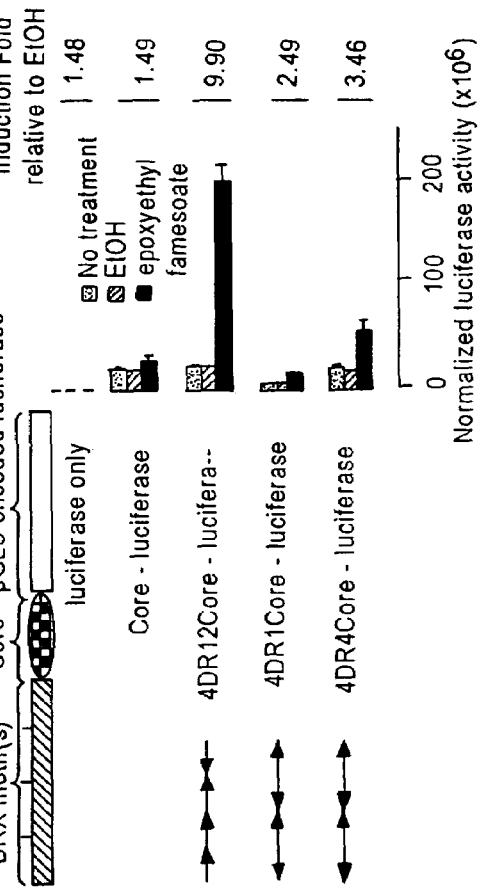
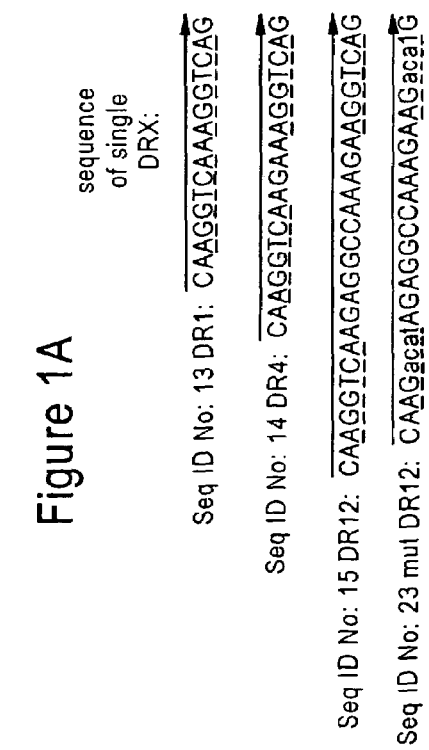

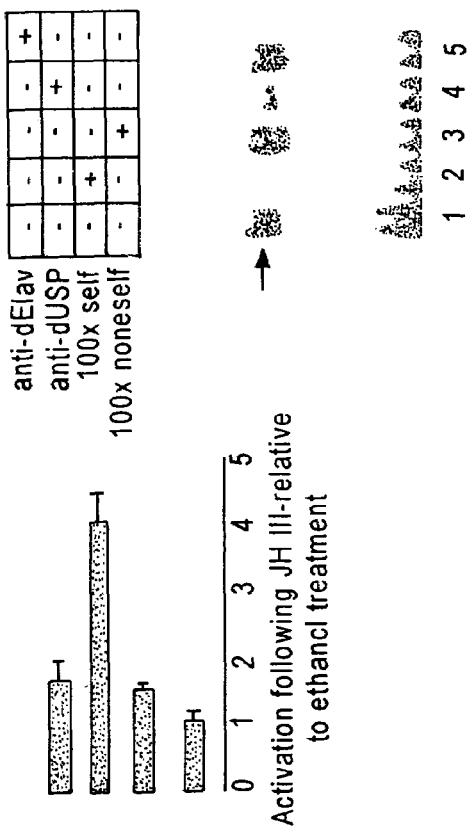
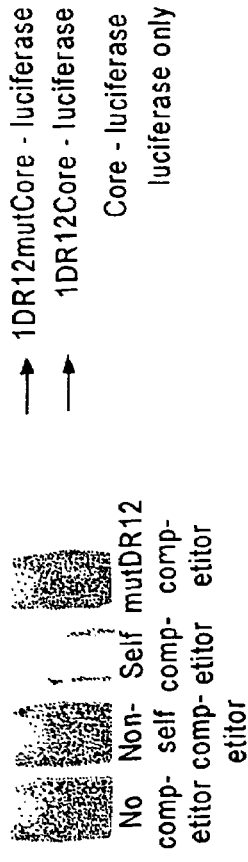
Figure 2A
Figure 2B
Figure 2C

Panel C - Drosophila USP

Panel D - Overlay

Replace two proline residues at the end of on helix 12 with two tryptophanes

SEQUENCE LISTING

```
<160> NUMBER OF SEQ ID NOS: 23

<210> SEQ ID NO 1
<211> LENGTH: 2488
<212> TYPE: DNA
<213> ORGANISM: Drosophila melanogaster

<400> SEQUENCE: 1
aaaaatgtcg acgcgaaaaa aggtatttat tcattagtca gaaagtctgg cattctttgt      60
ttgttggtaa aaagcgcaat tgtttggagg cgagcgaata aagtgcgctg ctccatcggc     120
tcaagattat gtaaatgcag caacgacccc accaacaacg aaactgcaac ctgctccact     180
tggcccaacg gaccaatagc ggacggacgg acacggtggc gttggcaaag tgaaacccca     240
acagagaggc gaaagcgagc caagacacac cacatacaca cgaagagaac gagcaagaag     300
aaaccggtag gcggaggagg cgctgccccc agttcctcca atatacccag caccacatca     360
caagcccagg atggacaact gcgaccagga cgccagcttt cggctgagcc acatcaagga     420
ggaggtcaag ccggacatct cgcagctgaa cgacagcaac aacagcagct tttcgcccaa     480
ggccgagagt cccgtgccct tcatgcaggc catgtccatg gtccacgtgc tgcccggctc     540
caactccgcc agctccaaca acaacagcgc tggagatgcc caaatggcgc aggcgcccaa     600
ttcggctgga ggctctgccg ccgctgcagt ccagcagcag tatccgccta accatccgct     660
gagcggcagc aagcacctct gctctatttg cggggatcgg gccagtggca agcactacgg     720
cgtgtacagc tgtgagggct gcaagggctt ctttaaacgc acagtgcgca aggatctcac     780
atacgcttgc agggagaacc gcaactgcat catagacaag cggcagagga accgctgcca     840
gtactgccgc taccagaagt gcctaacctg cggcatgaag cgcgaagcgg tccaggagga     900
gcgtcaacgc ggcgcccgca atgcggcggg taggctcagc gccagcggag gcggcagtag     960
cggtccaggt tcggtaggcg gatccagctc tcaaggcgga ggaggaggag gcggcgtttc    1020
tggcggaatg ggcagcggca acggttctga tgacttcatg accaatagcg tgtccaggga    1080
tttctcgatc gagcgcatca tagaggccga gcagcgagcg gagacccaat gcggcgatcg    1140
tgcactgacg ttcctgcgcg ttggtcccta ttccacagtc cagccggact acaagggtgc    1200
cgtgtcggcc ctgtgccaag tggtcaacaa acagctcttc cagatggtcg aatacgcgcg    1260
catgatgccg cactttgccc aggtgccgct ggacgaccag gtgattctgc tgaaagccgc    1320
```

```
ttggatcgag ctgctcattg cgaacgtggc ctggtgcagc atcgtttcgc tggatgacgg    1380
cggtgccggc ggcgggggcg gtggactagg ccacgatggc tcctttgagc gacgatcacc    1440
gggccttcag ccccagcagc tgttcctcaa ccagagcttc tcgtaccatc gcaacagtgc    1500
gatcaaagcc ggtgtgtcag ccatcttcga ccgcatattg tcggagctga gtgtaaagat    1560
gaagcggctg aatctcgacc gacgcgagct gtcctgcttg aaggccatca tactgtacaa    1620
cccggacata cgcgggatca agagccgggc ggagatcgag atgtgccgcg agaaggtgta    1680
cgcttgcctg gacgagcact gccgcctgga acatccgggc gacgatggac gctttgcgca    1740
actgctgctg cgtctgcccg ctttgcgatc gatcagcctg aagtgccagg atcacctgtt    1800
cctcttccgc attaccagcg accggccgct ggaggagctc tttctcgagc agctggaggc    1860
gccgccgcca cccggcctgg cgatgaaact ggagtagggt cccgactcta aagtctcccc    1920
cgttctccat ccgaaaaatg tttcattgtg attgcgtttg tttgcatttc tcctctctat    1980
cccttatacc ctacaaaagc cccctaatat tacgcaaaat gtgtatgtaa ttgtttattt    2040
ttttttattt acctaatatt attattatta ttgatataga aaatgttttc cttaagatga    2100
agattagcct cctcgacgtt tatgtcccag taaacgaaaa acaaacaaaa tccaaaactt    2160
gaaaagaaca caaacacga acgagaaaat gcacacaagc aaagtaaaag taaaagttaa    2220
actaaagcta aacgagtaaa gatattaaaa taacggttaa aattaatgca tagttatgat    2280
ctacagacgt atgtaaacat acaaattcag cataaatata tatgtcagca ggcgcatatc    2340
tgcggtgctg gccccgttct aaatcaattg taattacttt ttaacataaa tttacccaaa    2400
acgttatcaa ttagatgcga gatacaaaaa tcaccgacga aaaccaacaa aatatatcta    2460
tgtataaaaa atataaactg cataacaa                                       2488
```

<210> SEQ ID NO 2
<211> LENGTH: 508
<212> TYPE: PRT
<213> ORGANISM: Drosophila melanogaster

<400> SEQUENCE: 2

```
Met Asp Asn Cys Asp Gln Asp Ala Ser Phe Arg Leu Ser His Ile Lys
1               5                   10                  15

Glu Glu Val Lys Pro Asp Ile Ser Gln Leu Asn Asp Ser Asn Asn Ser
            20                  25                  30

Ser Phe Ser Pro Lys Ala Glu Ser Pro Val Pro Phe Met Gln Ala Met
        35                  40                  45

Ser Met Val His Val Leu Pro Gly Ser Asn Ser Ala Ser Ser Asn Asn
    50                  55                  60

Asn Ser Ala Gly Asp Ala Gln Met Ala Gln Ala Pro Asn Ser Ala Gly
65                  70                  75                  80

Gly Ser Ala Ala Ala Val Gln Gln Gln Tyr Pro Pro Asn His Pro
            85                  90                  95

Leu Ser Gly Ser Lys His Leu Cys Ser Ile Cys Gly Asp Arg Ala Ser
            100                 105                 110

Gly Lys His Tyr Gly Val Tyr Ser Cys Glu Gly Cys Lys Gly Phe Phe
        115                 120                 125

Lys Arg Thr Val Arg Lys Asp Leu Thr Tyr Ala Cys Arg Glu Asn Arg
    130                 135                 140

Asn Cys Ile Ile Asp Lys Arg Gln Arg Asn Arg Cys Gln Tyr Cys Arg
145                 150                 155                 160
```

```
Tyr Gln Lys Cys Leu Thr Cys Gly Met Lys Arg Ala Val Gln Glu
                165                 170                 175

Glu Arg Gln Arg Gly Ala Arg Asn Ala Ala Gly Arg Leu Ser Ala Ser
            180                 185                 190

Gly Gly Gly Ser Ser Gly Pro Gly Ser Val Gly Ser Ser Ser Gln
            195                 200                 205

Gly Gly Gly Gly Gly Gly Val Ser Gly Met Gly Ser Gly Asn
        210                 215                 220

Gly Ser Asp Asp Phe Met Thr Asn Ser Val Ser Arg Asp Phe Ser Ile
225                 230                 235                 240

Glu Arg Ile Ile Glu Ala Gln Arg Ala Glu Thr Gln Cys Gly Asp
                245                 250                 255

Arg Ala Leu Thr Phe Leu Arg Val Gly Pro Tyr Ser Thr Val Gln Pro
            260                 265                 270

Asp Tyr Lys Gly Ala Val Ser Ala Leu Cys Gln Val Val Asn Lys Gln
        275                 280                 285

Leu Phe Gln Met Val Glu Tyr Ala Arg Met Met Pro His Phe Ala Gln
    290                 295                 300

Val Pro Leu Asp Asp Gln Val Ile Leu Leu Lys Ala Ala Trp Ile Glu
305                 310                 315                 320

Leu Leu Ile Ala Asn Val Ala Trp Cys Ser Ile Val Ser Leu Asp Asp
                325                 330                 335

Gly Gly Ala Gly Gly Gly Gly Gly Leu Gly His Asp Gly Ser Phe
            340                 345                 350

Glu Arg Arg Ser Pro Gly Leu Gln Pro Gln Leu Phe Leu Asn Gln
        355                 360                 365

Ser Phe Ser Tyr His Arg Asn Ser Ala Ile Lys Ala Gly Val Ser Ala
    370                 375                 380

Ile Phe Asp Arg Ile Leu Ser Glu Leu Ser Val Lys Met Lys Arg Leu
385                 390                 395                 400

Asn Leu Asp Arg Arg Glu Leu Ser Cys Leu Lys Ala Ile Ile Leu Tyr
                405                 410                 415

Asn Pro Asp Ile Arg Gly Ile Lys Ser Arg Ala Glu Ile Glu Met Cys
            420                 425                 430

Arg Glu Lys Val Tyr Ala Cys Leu Asp Glu His Cys Arg Leu Glu His
        435                 440                 445

Pro Gly Asp Asp Gly Arg Phe Ala Gln Leu Leu Leu Arg Leu Pro Ala
450                 455                 460

Leu Arg Ser Ile Ser Leu Lys Cys Gln Asp His Leu Phe Leu Phe Arg
465                 470                 475                 480

Ile Thr Ser Asp Arg Pro Leu Glu Glu Leu Phe Leu Glu Gln Leu Glu
                485                 490                 495

Ala Pro Pro Pro Gly Leu Ala Met Lys Leu Glu
            500                 505

<210> SEQ ID NO 3
<211> LENGTH: 61
<212> TYPE: DNA
<213> ORGANISM: Trichoplusia ni granulovirus

<400> SEQUENCE: 3
gaccaattaa taggtgacct gcgataaaaa ttacctataa atatgtgatg ttgctggatt    60
g                                                                    61
```

```
<210> SEQ ID NO 4
<211> LENGTH: 134
<212> TYPE: DNA
<213> ORGANISM: Trichoplusia ni granulovirus

<400> SEQUENCE: 4
cgagaggtta tcgcccaata caacaacaat gataatgacg tgcaagcaga taatagtgaa      60
aaaataacag atactagagt ataaaaaggg gatgctggga gtggacaggc acagtcgtgg     120
tgtggcagca aaca                                                       134

<210> SEQ ID NO 5
<211> LENGTH: 69
<212> TYPE: DNA
<213> ORGANISM: Trichoplusia ni granulovirus

<400> SEQUENCE: 5
tcagtataaa aagggggtgca ttctcggtaa gagtacagtt gaactcacat cgagttaact     60
ccacgatga                                                              69

<210> SEQ ID NO 6
<211> LENGTH: 63
<212> TYPE: DNA
<213> ORGANISM: Trichoplusia ni granulovirus

<400> SEQUENCE: 6
taagggtagt ataaaaaggc gatcaatcat tgacaaacag tttgcagcag gctgtgggaa     60
cga                                                                    63

<210> SEQ ID NO 7
<211> LENGTH: 15
<212> TYPE: DNA
<213> ORGANISM: Artificial Sequence
<220> FEATURE:
<223> OTHER INFORMATION: Chemically synthesized

<400> SEQUENCE: 7
gaggtcaatg acctc                                                       15

<210> SEQ ID NO 8
<211> LENGTH: 24
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (7)..(18)
<223> OTHER INFORMATION: N is A, T, G or C
<220> FEATURE:
<221> NAME/KEY: misc_feature
<222> LOCATION: (8)..(18)
<223> OTHER INFORMATION: Any one of these 11 N's may or may not be
      present

<400> SEQUENCE: 8
aggtcannnn nnnnnnnnag gtca                                             24

<210> SEQ ID NO 9
<211> LENGTH: 24
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
```

```
<222> LOCATION: (7)..(18)
<223> OTHER INFORMATION: N = A, T, G or C
<220> FEATURE:
<221> NAME/KEY: misc_feature
<222> LOCATION: (8)..(18)
<223> OTHER INFORMATION: Any one of these 11 N's may or may not be
      present

<400> SEQUENCE: 9
tgacctnnnn nnnnnnnntg acct                                           24

<210> SEQ ID NO 10
<211> LENGTH: 13
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (7)..(7)
<223> OTHER INFORMATION: n is a, c, g, or t

<400> SEQUENCE: 10
aggtcanagg tca                                                       13

<210> SEQ ID NO 11
<211> LENGTH: 26
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 11
aggtcanagg tcaaggtcan aggtca                                         26

<210> SEQ ID NO 12
<211> LENGTH: 26
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 12
aggtcanagg tcatgacctn tgacct                                         26

<210> SEQ ID NO 13
<211> LENGTH: 16
<212> TYPE: DNA
<213> ORGANISM: Artificial Sequence
<220> FEATURE:
<223> OTHER INFORMATION: Chemically synthesized

<400> SEQUENCE: 13
caaggtcaaa ggtcag                                                    16
```

<210> SEQ ID NO 14
<211> LENGTH: 19
<212> TYPE: DNA
<213> ORGANISM: Artificial Sequence
<220> FEATURE:
<223> OTHER INFORMATION: Chemically synthesized

<400> SEQUENCE: 14
caaggtcaag aaaggtcag                                        19

<210> SEQ ID NO 15
<211> LENGTH: 27
<212> TYPE: DNA
<213> ORGANISM: Artificial Sequence
<220> FEATURE:
<223> OTHER INFORMATION: Chemically synthesized

<400> SEQUENCE: 15
caaggtcaag aggccaaaga aggtcag                               27

<210> SEQ ID NO 16
<211> LENGTH: 27
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (9)..(20)
<223> OTHER INFORMATION: n is a, c, g, or t

<400> SEQUENCE: 16
caaggtcann nnnnnnnnnn aggtcag                               27

<210> SEQ ID NO 17
<211> LENGTH: 36
<212> TYPE: DNA
<213> ORGANISM: Artificial Sequence
<220> FEATURE:
<223> OTHER INFORMATION: Chemically synthesized

<400> SEQUENCE: 17
ggtaccgagc tcttacgcgt gctagcccgg gctcga                     36

<210> SEQ ID NO 18
<211> LENGTH: 40
<212> TYPE: DNA
<213> ORGANISM: Artificial Sequence
<220> FEATURE:
<223> OTHER INFORMATION: Chemically synthesized

<400> SEQUENCE: 18
cggtatttca caccgcacat ggtgcactct cagtacaatc                 40

<210> SEQ ID NO 19
<211> LENGTH: 43
<212> TYPE: DNA
<213> ORGANISM: Artificial Sequence
<220> FEATURE:
<223> OTHER INFORMATION: Chemically synthesized

<400> SEQUENCE: 19
gtgccaagtg gtcaacaaag cgctcttcca gatggtcgaa tac             43

<210> SEQ ID NO 20

-continued

```
<211> LENGTH: 51
<212> TYPE: DNA
<213> ORGANISM: Artificial Sequence
<220> FEATURE:
<223> OTHER INFORMATION: Chemically synthesized

<400> SEQUENCE: 20
gcgatcgatc agcctgaagg cccaggatct cctgttcctc ttccgcatta c         51

<210> SEQ ID NO 21
<211> LENGTH: 51
<212> TYPE: DNA
<213> ORGANISM: Artificial Sequence
<220> FEATURE:
<223> OTHER INFORMATION: Chemically synthesized

<400> SEQUENCE: 21
ctttctcgag cagctggagg cgtggtggcc acccggcctg gcgatgaaac t         51

<210> SEQ ID NO 22
<211> LENGTH: 89
<212> TYPE: DNA
<213> ORGANISM: Trichoplusia ni granulovirus

<400> SEQUENCE: 22
cgtgtcggtg ccgctgctgg ggtcgcgcgc cacatatatg cgtgcgagga gcgcgcgccg    60
gcagtgcggc gtgcgacccc gaccagaca                                     89

<210> SEQ ID NO 23
<211> LENGTH: 27
<212> TYPE: DNA
<213> ORGANISM: Artificial Sequence
<220> FEATURE:
<223> OTHER INFORMATION: Chemically synthesized

<400> SEQUENCE: 23
caagacatag aggccaaaga agacatg                                       27
```

US 7,259,254 B2

MUTANTS AND ASSAY SYSTEM TO IDENTIFY USP/RXR LIGANDS

This specification claims the benefit of and incorporates by reference U.S. Provisional Patent Application 60/428,282 filed Nov. 22, 2002. Additionally, all references and publications referred to herein are incorporated by reference for their entirety, including Xu et al. (2002) Eur. J. Biochem., 269:6026-6036.

BACKGROUND OF THE INVENTION

1. Field of the Invention

This invention relates to the fields of drug discovery and pest control. Specifically it provides biochemical tools and assays that enable the user to identify to chemical compounds that are effective in activating or blocking particular hormone-dependent regulatory pathways in various organisms.

2. Background

Nuclear hormone receptors are a primary transduction mechanism through which extracellular hormonal signals are transduced into genetic regulation of metabolic pathways and developmental programs. The past two decades have seen the steady identification of mammalian receptors of well-known ligands such as steroids, thyroid hormone, all-trans retinoic acid (RA) as well as the identification of endogenous ligands for initially orphaned receptors. Similarly, steroid nuclear receptors in invertebrate models of transcriptional regulation, such as the *Drosophila melanogaster* ecdysteroid receptor (dEcR), were isolated a decade ago and used to develop important concepts in cellular hormonal signaling.

In parallel to the search for receptors that can be activated by known ligands, has been the search for ligands of orphan receptors of the steroid nuclear receptor superfamily, whose natural ligands are unknown. The biological relevance of identification of agonistic or antagonistic ligands for orphan receptors is several fold. First, the ability of a chemical structure to fit into the ligand-binding pocket of an orphan receptor and thereby transcriptionally activate the orphan receptor, would raise the possibility that the orphan receptor ligand-binding pocket has a conformation enabling it to bind with and be activated by a natural ligand of complementary structure. Second, the identification of ligands that activate or antagonize an orphan receptor would aid the discovery of regulatory pathways in which the receptor participates. Finally, transcriptional agonists and antagonists of orphan receptors provide leads to pharmacologically or agri-chemically significant structures that, through the orphan receptor, can selectively intercede in disease pathways or insect specific hormonal regulation.

In an effort to reduce the exposure of humans and other non-target organisms to the toxic effects of pesticides, major commercial efforts are being made to identify chemicals that selectively disrupt the hormonal processes that are specific to insects (e.g., humans do not have an exoskeleton that is periodically shed, nor do humans go through metamorphosis, as insects do). Two particular hormonal targets for these commercial efforts are the insect hormones that drive molting and metamorphosis: ecdysone and juvenile hormone. Some commercial compounds mimicking these hormones have already been developed, however, the concern remains that compounds interfering with insect hormonal signaling may cross-react with mammalian hormone receptors. For example, a metabolite of the juvenile hormone mimic methoprene, binds the human RXR receptor, see Dhadialla et al., Annual Review of Entomology, 43:545-569 (1998); Harmon et al. Proc Natl. Acad. Sci. USA., 92:6157-6160 (1995).

Identification of chemical compounds that bind to the ligand-binding pocket of ultraspiracle, the *Drosophila* RXR ortholog, has been stymied in part by difficulty in demonstrating specific binding of a test compound to the purified receptor. Specifically, it has been difficult to demonstrate ligand binding because there has been no efficient assay for detecting the conformational changes in a receptor upon interaction between a ligand and a USP and RXR. Indeed, the current paradigm expressed in most published models for USP function is that USP does not bind to any ligand in exerting its regulatory functions. Lezzi et al., (1999) Archives of Insect Biochemistry and Physiology, 41:99-106. A demonstration that endogenous USP can become activated upon binding to an agonist would have major implications for the current paradigms of hormone action in invertebrates. Jones et al., Proc Natl. Acad. Sci. USA., 94:13499-13503 (1997).

The orthology between invertebrate USP and vertebrate RXR indicates that the USP ligand-binding pocket may be arranged so as to be susceptible to binding and activation by a terpenoid-related ligand. In a previous report, it was observed that the application of methyl epoxyfarnesoate to cells activated a transfected reporter construct containing direct repeat elements to which recombinant USP bound in gel shift assay. However, these indirect experiments did not address whether methyl epoxyfarnesoate actually binds to the ligand-binding pocket of the receptor, nor whether endogenous USP in the transfected cells actually binds to the direct repeat elements, nor do they address whether methyl epoxyfarnesoate-activation of the reporter is dependent upon liganded USP, all of which are crucial underpinnings to the concept of the USP ligand-binding pocket as a viable target for experimental or practical agonistic or antagonistic ligands.

SUMMARY OF THE INVENTION

The invention relates to mutant nuclear hormone receptors that have either altered fluorescence properties and/or dominant negative activity.

One aspect of the invention relates to nucleic acids that encode mutant nuclear hormone receptors, in which particular amino acid residues are substituted with respect to wild type, so as to be able to detect ligand binding to the mutant receptor by either a change in a physical property of the mutant receptor and/or an transcriptional induction of a nuclear hormone receptor construct.

One embodiment of this aspect of the invention relates to an isolated nucleic acid capable of hybridizing to SEQ ID NO: 1 under stringent conditions and encoding a protein having a tryptophan residue in a first position corresponding to position 477 of SEQ ID NO: 2 and a tryptophan residue in a second position corresponding to position 479 of SEQ ID NO: 2, which upon binding an epoxy farnesoid-like ligand results in transcriptional activation of a nuclear hormone receptor reporter construct.

Another embodiment of this aspect of the invention relates to an isolated nucleic acid capable of hybridizing to SEQ ID NO: 1 under stringent conditions and encoding a protein having a tryptophan residue in a first position corresponding to position 477 of SEQ ID NO: 2, which upon binding an epoxy farnesoid-like ligand results in transcriptional activation of a nuclear hormone receptor reporter construct.

Another embodiment of this aspect of the invention relates to an isolated nucleic acid capable of hybridizing to SEQ ID NO: 1 under stringent conditions and encoding a protein having a tryptophan residue in a first position corresponding to position 479 of SEQ ID NO: 2, which upon binding an epoxy farnesoid-like ligand results in transcriptional activation of a nuclear hormone receptor reporter construct.

Another embodiment of this aspect of the invention relates to an isolated nucleic acid capable of hybridizing to SEQ ID NO: 1 under stringent conditions and encoding a protein having a tryptophan residue in a first position corresponding to position 302 of SEQ ID NO: 2, which upon binding an epoxy farnesoid-like ligand results in transcriptional activation of a nuclear hormone receptor reporter construct.

Another embodiment of this aspect of the invention relates to an isolated nucleic acid capable of hybridizing to SEQ ID NO: 1 under stringent conditions and encoding a protein having a tryptophan residue in a first position corresponding to position 315 of SEQ ID NO: 2, which upon binding an epoxy farnesoid-like ligand results in transcriptional activation of a nuclear hormone receptor reporter construct.

Another embodiment of this aspect of the invention relates to an isolated nucleic acid capable of hybridizing to SEQ ID NO: 1 under stringent conditions and encoding a protein having a phenylalanine residue in a first position corresponding to position 318 of SEQ ID NO: 2, which upon binding an epoxy farnesoid-like ligand results in transcriptional activation of a nuclear hormone receptor reporter construct.

Another embodiment of this aspect of the invention relates to an isolated nucleic acid capable of hybridizing to SEQ ID NO: 1 under stringent conditions and encoding a protein having a phenylalanine residue in a first position corresponding to position 328 of SEQ ID NO: 2, which upon binding an epoxy farnesoid-like ligand results in transcriptional activation of a nuclear hormone receptor reporter construct.

Another embodiment of this aspect of the invention relates to an isolated nucleic acid capable of hybridizing to SEQ ID NO: 1 under stringent conditions and encoding a protein having a phenylalanine residue in a first position corresponding to position 318 of SEQ ID NO: 2, and a phenylalanine residue in a second position corresponding to position 328 of SEQ ID NO: 2, which upon binding an epoxy farnesoid-like ligand results in transcriptional activation of a nuclear hormone receptor reporter construct.

Another embodiment of this aspect of the invention relates to an isolated nucleic acid capable of hybridizing to SEQ ID NO: 1 under stringent conditions and encoding a protein having an tryptophan residue in a first position corresponding to position 498 of SEQ ID NO: 2, a tryptophan residue in a second position corresponding to position 499 of SEQ ID NO: 2, and phenylalanine residue in a third position corresponding to position 318 of SEQ ID NO: 2, which upon binding an epoxy farnesoid-like ligand results in transcriptional activation of a nuclear hormone receptor reporter construct.

Another embodiment of this aspect of the invention relates to an isolated nucleic acid capable of hybridizing to SEQ ID NO: 1 under stringent conditions and encoding a protein having an tryptophan residue in a first position corresponding to position 498 of SEQ ID NO: 2, a tryptophan residue in a second position corresponding to position 499 of SEQ ID NO: 2, and phenylalanine residue in a third position corresponding to position 328 of SEQ ID NO: 2, which upon binding an epoxy farnesoid-like ligand results in transcriptional activation of a nuclear hormone receptor reporter construct.

Another embodiment of this aspect of the invention relates to an isolated nucleic acid capable of hybridizing to SEQ ID NO: 1 under stringent conditions and encoding a protein having an tryptophan residue in a first position corresponding to position 498 of SEQ ID NO: 2, a tryptophan residue in a second position corresponding to position 499 of SEQ ID NO: 2, and phenylalanine residue in a third position corresponding to position 318 of SEQ ID NO: 2, and phenylalanine residue in a fourth position corresponding to position 328 of SEQ ID NO: 2, which upon binding an epoxy farnesoid-like ligand results in transcriptional activation of a nuclear hormone receptor reporter construct.

Another aspect of the invention relates to a nucleic acids that encode dominant negative mutant nuclear hormone receptors.

One embodiment of this aspect of the invention relates to an isolated nucleic acid capable of hybridizing to SEQ ID NO: 1 under stringent conditions and encoding a protein having an phenylalanine residue in a first position corresponding to position 318 of SEQ ID NO: 2, which is a dominant negative nuclear hormone receptor.

One embodiment of this aspect of the invention relates to an isolated nucleic acid capable of hybridizing to SEQ ID NO: 1 under stringent conditions and encoding a protein having a phenylalanine residue in a first position corresponding to position 318 of SEQ ID NO: 2, and a phenylalanine residue in a second position corresponding to position 328 of SEQ ID NO: 2, which is a dominant negative nuclear hormone receptor.

One embodiment of this aspect of the invention relates to an isolated nucleic acid capable of hybridizing to SEQ ID NO: 1 under stringent conditions and encoding a protein having an tryptophan residue in a first position corresponding to position 498 of SEQ ID NO: 2, a tryptophan residue in a second position corresponding to position 499 of SEQ ID NO: 2, and phenylalanine residue in a third position corresponding to position 318 of SEQ ID NO: 2, which is a dominant negative nuclear hormone receptor.

One embodiment of this aspect of the invention relates to an isolated nucleic acid capable of hybridizing to SEQ ID NO: 1 under stringent conditions and encoding a protein having an tryptophan residue in a first position corresponding to position 498 of SEQ ID NO: 2, a tryptophan residue in a second position corresponding to position 499 of SEQ ID NO: 2, and phenylalanine residue in a third position corresponding to position 318 of SEQ ID NO: 2, and phenylalanine residue in a fourth position corresponding to position 328 of SEQ ID NO: 2, which is a dominant negative nuclear hormone receptor.

Another embodiment of this aspect of the invention relates to an isolated nucleic acid capable of hybridizing to SEQ ID NO: 1 under stringent conditions and encoding a protein having an alanine residue in a first position corresponding to position 472 of SEQ ID NO: 2 and leucine residue in a second position corresponding to position 475 of SEQ ID NO: 2, which is a dominant negative nuclear hormone receptor.

Another embodiment of this aspect of the invention relates to an isolated nucleic acid capable of hybridizing to SEQ ID NO: 1 under stringent conditions and encoding a protein having an arginine residue in a first position corresponding to position 302 of SEQ ID NO: 2, which is a dominant negative nuclear hormone receptor.

Another embodiment of this aspect of the invention relates to an isolated nucleic acid capable of hybridizing to SEQ ID NO: 1 under stringent conditions and encoding a protein having an arginine residue in a first position corresponding to position 293 of SEQ ID NO: 2, which is a dominant negative nuclear hormone receptor.

Another embodiment of this aspect of the invention relates to an isolated nucleic acid capable of hybridizing to SEQ ID NO: 1 under stringent conditions and encoding a protein having an alanine residue in a first position corresponding to position 288 of SEQ ID NO: 2, which is a dominant negative nuclear hormone receptor.

Another embodiment of this aspect of the invention relates to an isolated nucleic acid capable of hybridizing to SEQ ID NO: 1 under stringent conditions and encoding a protein having an alanine residue in a first position corresponding to position 366 of SEQ ID NO: 2, which is a dominant negative nuclear hormone receptor.

Another embodiment of this aspect of the invention relates to an isolated nucleic acid capable of hybridizing to SEQ ID NO: 1 under stringent conditions and encoding a protein having an alanine residue in a first position corresponding to position 366 of SEQ ID NO: 2 and an alanine residue in a second position corresponding to position 288 of SEQ ID NO: 2 which is a dominant negative nuclear hormone receptor.

Another aspect of the invention relates to a method identifying ligands of nuclear hormone receptors comprising: contacting a mutant nuclear hormone receptor protein with a candidate ligand; and determining whether there is a change in a physical property of the protein or a change in the transcriptional activity of the protein.

In one embodiment of this aspect of the invention, the protein is a mutant USP receptor. In another embodiment, the protein is a mutant RXR receptor. In yet a further the embodiment, the ligand causes a change in the fluorescence properties and/or transcriptional activity the mutant USP receptor mutant nuclear hormone but not in the mutant RXR receptor.

Another aspect of the invention relates to a nuclear hormone receptor response element denoted by the formula YDRX comprising a direct repeat (DR) comprising two half sites separated by X nucleic acid bases; wherein a forward DR sequence is 5'-AGGTCA(N)$_x$AGGTCA-3' (SEQ ID NO: 8) and a reverse DR sequence is 5'-TGACCT(N)$_x$TGACCT-3' (SEQ ID NO: 9); wherein the element comprises at least one DR oriented in either a forward or reverse orientation; wherein Y equals 1 to 8 forward and/or reverse direct repeats; and X equals 1 to about 12.

Another aspect of the invention relates to nuclear hormone receptor reporter construct comprising a nuclear hormone receptor response element, a promoter and a reporter nucleic acid sequence operably linked to one another; wherein the hormone receptor response element denoted by the formula YDRX comprises a direct repeat (DR) comprising two half sites separated by X nucleic acid bases; wherein a forward DR sequence is 5'-AGGTCA(N)$_x$AGGTCA-3' (SEQ ID NO: 8) and a reverse DR sequence is 5'-TGACCT (N)$_x$TGACCT-3' (SEQ ID NO: 9); wherein the element comprises at least one DR oriented in either a forward or reverse orientation; wherein Y equals 1 to 8 forward and/or reverse direct repeats; and X equals 1 to about 12; and wherein the promoter is selected from the group consisting of JHE, BJHSP 1, Aryl, BJHSP2, and AJHSP1.

Additional advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. The present invention may be practiced without some or all of these specific details. In other instances, well known process operations have not been described in detail, in order not to unnecessarily obscure the present invention. Accordingly, the drawings and description are to be regarded as illustrative in nature, and not as restrictive.

BRIEF DESCRIPTION OF THE DRAWINGS

FIG. 1. Activation of transfected Core promoter reporter through DR12 nuclear hormone response element. (A) The sequences of single copies of DR1 (SEQ ID NO:13), DR4 (SEQ ID NO:14), DR12 (SEQ ID NO:15) and mutant DR12 (SEQ ID NO:23) enhancer elements, i.e. motifs, used in the nuclear hormone receptor response reporter constructs. Each half site is dashed underlined. Mutated residues are shown in lower case letters. (B) On the left are the designs of the vector construct encoding the luciferase reporter enzyme, of the vector construct containing the Core promoter reporter, and of the three vector constructs in which the Core promoter is preceded by four tandem copies either a DR1-, a DR4- or a DR12-based enhancer, with the orientation of each motif shown by the small arrows. On the right are the activations of the indicated nuclear hormone receptor response reporter construct in response to treatment of transfected cells with 75 μm methyl epoxyfarnesoate.

FIG. 2. Functional analysis of the DR12 motif. (A) Gel mobility shift assay, using Sf9 nuclear extracts, of the same single DR12 motif that was used as an enhancer in the cell transfection assay in (B). The shifted probe band was competitively displaced by 100× of the unlabelled DR12 motif (self), but was not competed with either by the same mutant DR12 motif as failed to act as an enhancer in cell transfection assay in B (mutDR12) or by the negative control polylinker sequence (nonself). (B) Activations of the indicated promoter reporter constructs in response to treatment of transfected cells with 75 μm methyl epoxyfarnesoate. (C) Intracellular USP binds to DR12 hormone response element. Gel mobility shift assay using Sf9 nuclear extracts (N.E.) and a $^{32}$P-labelled probe that is the four tandem DR12 motifs ('4DR12') shown in FIG. 1, performed as described in Jones et al. (2001) Insect Biochem. Mol. Biol. 32, 33-49. The USP in the Sf9 nuclear extract that is the major binding complex (small arrow) is displaced by the AB11 monoclonal antibody, just as we have previously shown is the effect of this antibody on recombinant dUSP binding to a DR12 probe Jones et al. (2001) Insect Biochem. Mol. Biol. 32, 33-49. The lack of similar effect by monoclonal antibody against the negative control nerve transcription factor (Elav) shows the specificity of the AB11 result.

DETAILED DESCRIPTION OF THE INVENTION

Figure 3A:
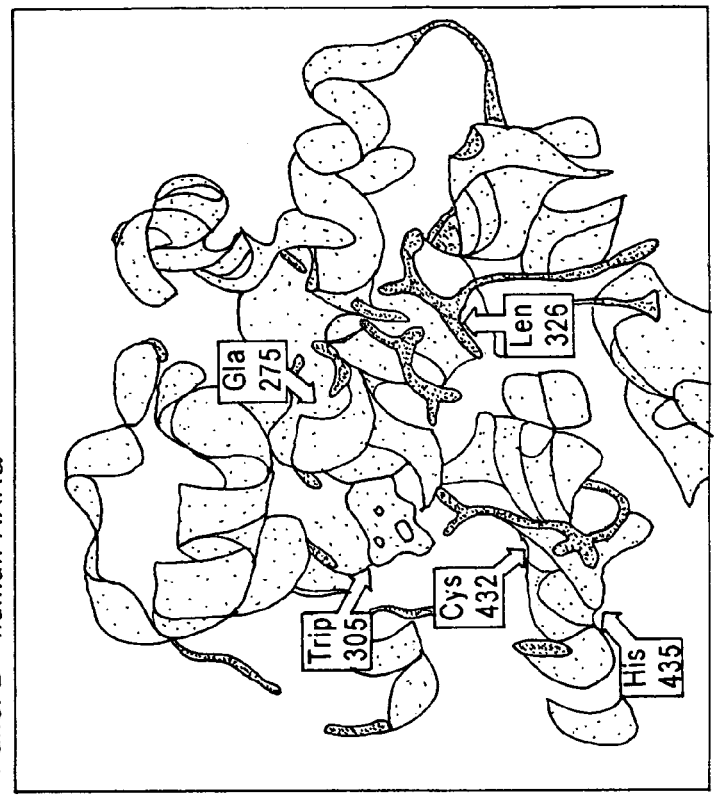
FIG. 3. Comparision of dUSP and hRXR ligand binding domains. (A) Selected contacts made between 9-cis RA and residues in the hRXRα ligand-binding pocket as determined from cocrystals (4.2 Å or less, from Egea et al. (2000) EMBO J. 19, 2592-2601). On the left is also shown a conformation of epoxyfarnesoic acid, exhibiting similarities between its structure and that of the terpenoid backbone and carboxyl group of 9-cis retinoic acid. (B and C) RASMOL-generated ribbon diagrams for the ligand-binding domains of the hRXRα and dUSP, respectively. (B) This shows in the hRXRα ligand-binding pocket the structure of the ligand 9-cis retinoic acid. (C) This shows methyl epoxyfarnesoic acid lain manually in the dUSP ligand-binding pocket with the carboxy and distal (epoxy) ends, respectively, situated in similar regions of the pocket as the carboxyl end and distal end of 9-cis RA in hRXRα. (D) An overlay of the dUSP and hRXR ribbon diagrams of B and C, with emphasis (white arrows) on the similar placement of Gln275, Trp305, Leu326, Cys432 and His435 in hRXR as compared to Gln288, Trp318, Leu367, Cys472 and His475 in dUSP.

Before describing the invention in greater detail the following definitions are set forth to illustrate and define the meaning and scope of the terms used to describe the invention herein:

As used herein, "wild type" refers to the nucleic acid or amino acid sequence of a particular protein as it most commonly occurs in nature as a normal functional protein. Nonetheless, it is elementary to one of skill in the art that such functional proteins have allelic variations. An allele is one of several alternate forms of a gene that can have the same locus on homologous chromosomes and are responsible for alternative traits. Some alleles are dominant over others. Such normal variation are encompassed within this term. Preferably, the wild type USP nucleic acid sequence is provided in SEQ ID NO: 1 and the wild type amino acid sequence is provided in SEQ ID NO: 2.

"Ligands" as defined herein are those compounds likely agonists or antagonists in the activation RXR and/or USP. Nuclear receptors are a family of proteins involved in key metabolic processes with great potential as targets for the treatment of significant diseases such as cancer, coronary heart disease through the regulation of serum cholesterol and diabetes. The nuclear receptor family contains a large group of transcription factors, with 49 members presently identified in the human genome. Many members of this family remain incompletely understood, both in terms of physiological role and activating ligands, but there is a high probability that these "orphan receptors" are good targets for drug development. As such, ligands may act as drug leads in the treatment of diseases where nuclear hormone receptors are thought to play a role such as in the. For example, a nuclear receptor LXR forms RXR/LXR to induce ABC1 reverse transporter of cholesterol to pump out cellular cholesterol, resulting in lowering dietary cholesterol. Still another nuclear receptor FXR forms RXR/FXR to induce cytochrome P450 hydroxylase CYP7A1 that metabolizes cholesterol to bile acid to again lower cholesterol level. Small molecular ligands that specifically bind to each nuclear receptor are novel drugs against hyperlipidemia. Ligands identified using the compositions and methods disclosed herein may be useful in the activation or inhibition of signal transduction mediated by USP, RXR or other nuclear hormone receptors. These ligands are mostly analogs of RXR compounds that bind to and activate RXR. Alternatively, the compositions and methods disclosed herein provide the ability to identify ligands useful in pest control that antagonize USP signaling while not cross-reacting with mammalian RXR signal transduction. Preferably, such compounds are terpenoid-related compounds. More preferably, ligands are structurally related to juvenile hormone III, retinoic acid, or epoxy farnesoid-like compounds.

"Activation" refers to the homo- or heterodimerization of nuclear hormone receptors to with their natural partners upon ligand binding to form a complex that is capable of binding a nuclear hormone receptor response element and inducing transcription of a gene operably linked thereto.

"Transcriptional activity" of a protein or nuclear hormone receptor as used herein refers to the ability of a nuclear hormone receptor to homo- or heterodimerize, bind a nuclear hormone receptor response element and induce the transcription of any nucleic acid operably linked thereto.

As used herein "RXR" refers to the retinoid X receptor (RXR) which is a member of the nuclear hormone receptor family of proteins. Such receptors are also transcription factors, binding hormone ligands and acting together with others in the superfamily to activate transcripts of hormone responsive genes. RXR plays a uniquely important role in differentiation, development, and homeostasis through its ability to serve as a heterodimeric partner to many other nuclear receptors. RXR is a ligand-dependent transcription factor. RXR is able to influence the activity of its partner receptors through the action of the ligand 9-cis retinoic acid. RXR contains two signature domains of nuclear receptor family proteins, i.e. DNA-binding domain and ligand binding domain (LBD). The endogenous ligand for RXR is 9-cis retinoic acid. RXR plays an important role in many fundamental biological process such as reproduction, cellular differentiation, bone development, hematopoesis and pattern formation during embryogenesis. RXR is also implicated in some pathological conditions as neoplastic formation and it is a potential target for cancer therapy.

As used herein, "USP" refers the *Drosophila melanogaster* protein Ultraspiracle. USP is a promiscuous factor, meaning it can dimerize with multiple partners. It is homologous to the vertebrate retinoid-X receptor, which demonstrates the ancient lineage of the nuclear receptor superfamily. Partnering the Ecdysone receptor for the molting hormone in insects, USP activates genes involved in molting. Another target is the larval serum protein-2 gene whose product accumulates in the fat body tissue. This implicates USP in the functioning of the fat body in larval flies (Antoniewski, 1994). The fat body serves as an energy store for high levels of activity and for reproduction. In contrast to RXR, prior to this disclosure, USP was not not known to have known high-affinity ligand and was thought to be a silent component in the heterodimeric complex with partner receptors such as the ecdysone receptor.

As used herein "mutant nuclear hormone receptors" as used herein refers to protein having specific amino acid substitutions with respect to wild type nuclear hormone receptors. In one embodiment, these mutations comprise amino acid substitutions that serve to give make changes in protein confirmation due to interaction with a putative ligand, more easily detectable by providing the protein with altered fluorescent properties. More preferably, amino acid substitutions are made in the ligand biding domain of the nuclear hormone receptors. Even more preferably, amino acids substitutions are made in the ligand binding domain of USP or RXR.

Whereas, ligand binding does not sufficiently modulate the fluorescence of wild type receptors to facilitate ligand binding detection, some of the mutant receptors disclosed herein have markedly different fluorescent profiles upon binding a ligand. The change in fluorescence of a mutant receptor upon ligand binding can be detected by such exemplary techniques as anisotropy, Fluorescence Resonance Energy Transfer (FRET), or circular dichroism. Preferably, changes in fluorescence emission (either the magnitude of emission or the blue-red shift in emission) of tryptophan residues in the mutant receptor are monitored, in order to detect binding to the ligand binding pocket of the test mutant receptor by chemical compounds that do not themselves significantly absorb the fluorescent light emitted by the receptor. Alternatively, changes in the anisotropy (rotational volume) of the mutant receptor are monitored in order to detect binding of chemical compounds to the ligand pocket whose effects on the receptor are to either promoter or inhibit the binding of two identical mutant molecules into a dimer pair, i.e., formation of "homodimer".

In another embodiment, mutant nuclear hormone receptors disclosed herein comprise amino acid substitutions that render the mutant to act as a "dominant negative." Dominant negative proteins exploit protein-protein interactions, i.e., the interactions between a mutated protein produced by a transgene and the related native protein inside the cell. The mutant protein forms a dimer with an integral part of a wild type endogenous protein molecule. The mutant protein interacts with a whole range of native compatible gene products. Preferably, the mutant homodimerizes or heterodimerizes with an endogenous wild type partner to form a complex following ligand or independent of ligand binding. Preferably, as opposed to a complex of wild type monomers, a complex of a mutant and its endogenous wild type partner will be incapable of initiating transcription at a hormone receptor response reporter gene. Assays for determining dominant negative activity may be found in Examples 6 and 7 as well as FIG. 4.

In yet another embodiment, mutant nuclear hormone receptors have both altered fluorescent properties upon ligand binding as well as dominant negative activity. For example, USP W318F is a weak dominant negative that by the elimination of the fluorescence emitting tryptophan from W318 also enables more sensitive tracking of the tracking of changes in fluorescence emitted by W328. W328F is not a dominant negative. However, elimination of the fluorescence emitting tryptophan from W328 enables more sensitive tracking of the in fluorescence emitted by W318. P498W/P499W is not a dominant negative, but is used to detect the movement of alpha helix 12. However, the P498W/P499W is not the most efficient fluorescent detector of movement of alpha helix 12 because of the additional fluorescence being contributed by the wild type residues W318 and W328. So, when either W318, W328 or both are mutated away as W318F and/or W328F, removal of their contributing "background" fluorescence enables the fluorescent signaling from P498W/P499W to be more sensitive, indicating movement of alpha helix 12.

A list of some of the mutants envisioned by the invention is summarized in Table 1 below:

| USP Mutant | Altered Fluorescence with Respect to Wild Type | Dominant Negative Activity |
|---|---|---|
| F477W | + | − |
| F479W | + | − |
| F477W/F479W | + | − |
| F302W | + | − |
| K315W | + | − |
| P498W/P499W | + | − |
| W318F | + | Weak Activity |
| W328F | + | − |
| W318F/W328F | + | Weak Activity |
| P498W/P499W/W318F | + | Weak Activity |
| P498W/P499W/W328F | + | − |
| P498W/P499W/ W318F/W328F | + | Weak Activity |
| C472A/H475L | − | + |
| F302R | − | + |
| V293R | − | + |
| L314R | − | + |
| Q288A | − | + |
| L366A | − | + |
| Q288A/L366A | − | + |

Amino acid residue positions "corresponding" to one another as used herein, refers to the fact that there are conserved amino acid residues among orthologous proteins or among structurally similar mutant receptors that are encoded by substantially identical nucleic acids. Corresponding amino acids may be the same amino acids or they may be differing amino acids sharing one or more characteristics with respect to charge, polarity, acidity, hydrophilicity, hydrophobicity, or size. Preferably, the USP mutations disclosed in Table 1 are made in corresponding amino acids of RXR and other nuclear hormone receptors.

Figure 3B:
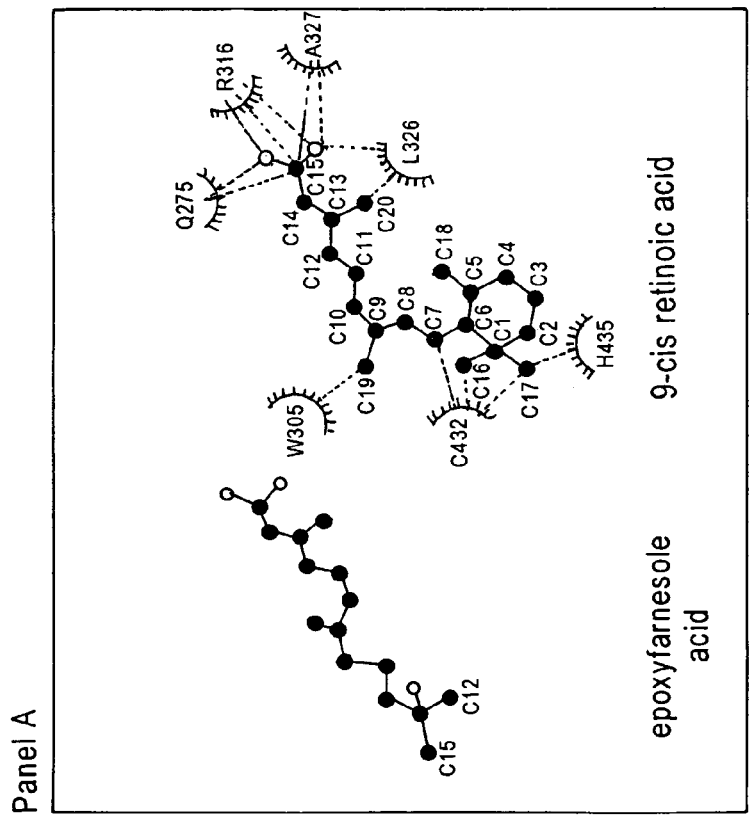
Figure 3C:
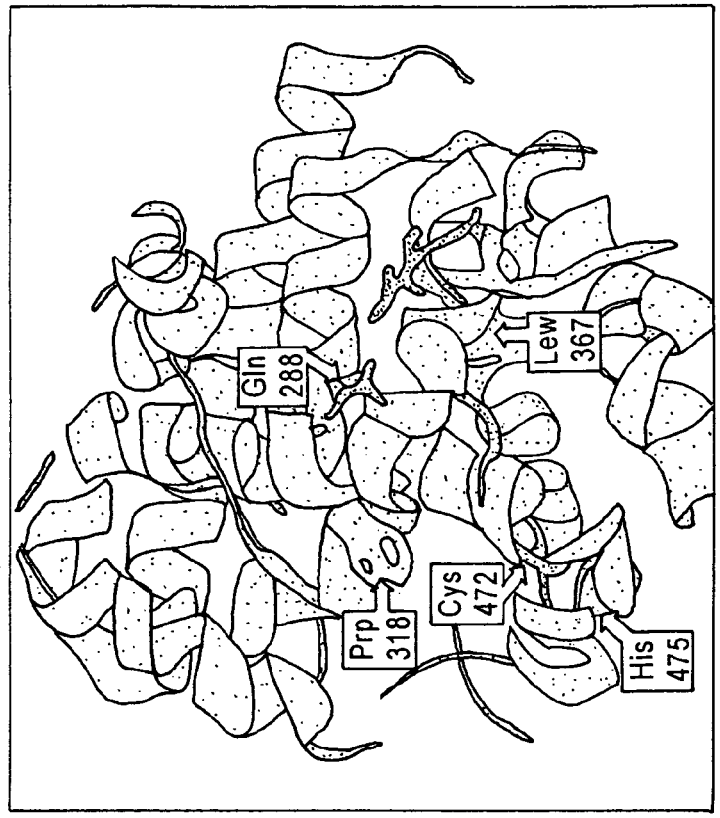
Figure 3D:
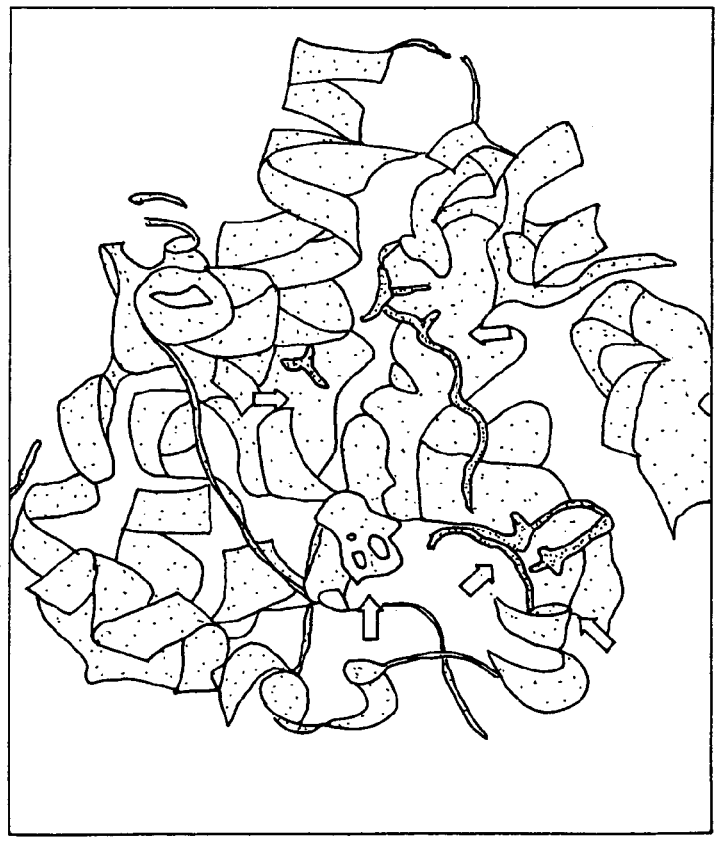

For exemplary purposes, in human RXR, Cys432 and His435 on α-helix 11 make contact with the distal end of the 9-cis RA ligand at two methyl branches (C 16, C 17) and also at the terpene backbone (FIGS. 3A,B). The corresponding two residues on α-helix 11 of *Drosophila* USP (Cys472 and His475) are highly conserved in other USPs Jones et al., Insect Biochem. Mol. Biol. 30, 671-679; and point into the ligand-binding pocket of USP crystal structures (FIG. 3C, Billas et al. (2000) J. Biol. Chem. 276, 7465-7474., Clayton et al. (2000) Proc. Natl. Acad. Sci. USA 98, 1549-1554). Other residues that contact 9-cis RA in hRXR are also conserved in identity and similar location in the ligand-binding pocket of USP, such as Gln288, Trp318 and Leu367 in USP corresponding to Gln275, Try305 and Leu326 of RXR, respectively (FIG. 3B-D). If an epoxy farnesoid-like ligand were to reside in the USP ligand-binding pocket along a similar trace as does 9-cis RA in RXR, then the terpene backbone and the methyl branches C 12 and C 15 at the distal end of the epoxy farnesoid ligand might be similarly placed to interact with His475 and Cys472 in USP, as does 9-cis RA interact with Cys432 and His435 in RXR (FIG. 3B-D).

USPs, which compared to RXR are unusual for their stretch of additional amino acids inserted after α-helix 5, have recently been cocrystalized with fortuitous phospholipid pseudoligands Billas et al. (2000) J. Biol. Chem. 276, 7465-7474., Clayton et al. (2000) Proc. Natl. Acad. Sci. USA 98, 1549-1554. These cocrystals had a relatively large total van der Waals volume of the USP ligand-binding pocket (=1300 Å$^3$), compared to the volume of JH III (259 Å$^3$ Bogan, et al., (1998) Nat. Struct. Biol. 5, 679-681). However, the volume of the PPARγ ligand-binding pocket (similar to that of USP, =1300 Å$^3$ Nolte et al. (1998) Nature 395, 137-143) is also much larger than that of its natural ligand 15-deoxy-Δ$^{12,14}$-prostaglandin J$_2$ (which has a volume similar to that of JH III, at 301 Å$^3$ Bogan, et al., (1998) Nat. Struct. Biol. 5, 679-681), yet this prostaglandin ligand is able to bind and transcriptionally activate the PPARγ; Kliewer et al (1995) Cell 83, 813-819. In addition, the volume of β-estradiol (which at 245-251 Å$^3$ is smaller than methyl epoxyfarnesoate; Bogan, et al., (1998) Nat. Struct. Biol. 5, 679-681), is approximately half the volume of the ligand-binding pocket of the estrogen receptor (450-500 Å$^3$; Brzozowski, et al (1997) Nature 389, 753-758., Shiau, et al (1998) Cell 95, 927-937), Yet, β-estradiol is nonetheless able to bind to and activate the estrogen receptor. Thus, PPARγ and the estrogen receptor demonstrate that endogenous compounds much smaller than the total ligand-binding pocket volume of a nuclear hormone receptor can and do serve as natural activating ligands. The recently crystallized PXR, which binds with, and is activated by, a variety of small and large ligands, also possesses a large 1300 Å$^3$ ligand-binding pocket [Watkins et al., (2001) Science 292, 2329-2333, and possesses an unusual additional stretch of amino acids that the authors postulated enables what would otherwise be a smaller PXR ligand-binding pocket to enlarge to accommodate a large ligand. Important in these considerations is whether there is a subregion in the ligand-binding pocket in which the local conformation corresponds well to the conformation of a particular small ligand. Although the overall volume of the ligand-binding pocket observed in the cocrystals of USP (=1300 Å$^3$) is much larger than that of hRXRα (=500 Å$^3$), the proximal subregion of the ligand-binding pocket of hRXR and USP are much more similar in volume and shape Clayton et al., (2000) Proc. Natl. Acad. Sci. USA 98, 1549-1554. The proximal subregion of each of the two receptors also has a similar placement of conserved amino acids that in hRXR interact with the terpenoid backbone of 9-cis RA (FIGS. 4A-D). In addition, 9-cis RA and methyl epoxyfarnesoate have similar van der Waals volumes of 291 and 258 Å$^3$, respectively Bogan, et al., (1998) Nat. Struct. Biol. 5, 679-681. These considerations suggest that methyl epoxyfarnesoate-like metabolites cannot be dismissed a priori as potential USP agonists, merely on the basis of comparison of the volume of methyl epoxyfarnesoate vs. the reported total volume of the USP ligand-binding pocket.

Given this disclosure exemplary corresponding amino acid positions in conjunction with standard protein alignment or 3-D modeling software common in the art, one of skill in the art would readily be able to determine the location of other corresponding amino acids residues inside and outside the ligand binding pocket of USP, RXR and other nuclear hormone receptors.

The term "nuclear hormone receptor response reporter construct" as used herein refers to a segment of DNA that comprises an operably linked nuclear hormone receptor response element, core promoter and reporter gene nucleic acid. These constructs are used to test whether ligand binding of a nuclear hormone receptor causes the receptor to induce transcription of its target gene as assayed by expression of the reporter gene nucleic acid or by the activity of the reporter gene nucleic acid translational product.

One embodiment of the nuclear hormone receptor response reporter construct has a an Aryl core (SEQ ID NO:

6) operably linked to a two copies of an EcRERF (SEQ ID NO: 7) nuclear hormone receptor response element. Preferably, other embodiments have a hormone receptor response element denoted by the formula YDRXZ having a direct repeat (DR) operably linked to a core promoter represented by SEQ ID NOs: 3, 4, 5, or 6.

The term "operably linked" refers to the linkage of a DNA segment to another DNA segment in such a way as to allow the segments to function in their intended manners. A DNA sequence encoding a gene product is operably linked to a regulatory sequence when it is ligated to the regulatory sequence, such as, for example, promoters, enhancers and/or silencers, in a manner which allows modulation of transcription of the DNA sequence, directly or indirectly. For example, a DNA sequence is operably linked to a promoter when it is ligated to the promoter downstream with respect to the transcription initiation site of the promoter, in the correct reading frame with respect to the transcription initiation site and allows transcription elongation to proceed through the DNA sequence. An enhancer, such as the envisaged nuclear hormone receptor response element, is operably linked to a promoter and a DNA sequence coding for a gene product when they are ligated to the DNA sequence in such a manner as to increase or decrease, respectively, the transcription of the DNA sequence. Enhancers and silencers may be located upstream, downstream or embedded within the coding regions of the DNA sequence. Linkage of DNA sequences to regulatory sequences is typically accomplished by ligation at suitable restriction sites or via adapters or linkers inserted in the sequence using restriction endonucleases known to one of skill in the art.

The term "nuclear hormone receptor response element" refers to a segment of DNA that is a target of ligand activated/homo- or heterodimerized nuclear hormone receptor which acts as an enhancer that when bound causes initiation of the formation of a transcriptional complex to being at the core promoter to which the element is operably linked. In one embodiment, a hormone receptor response element is denoted by the formula YDRXZ comprising a direct repeat (DR) having two half sites separated by X nucleic acid bases; wherein a forward DR sequence is 5'-AGGTCAN$_x$AGGTCA-3' (SEQ ID NO: 8) and a reverse DR sequence is 5'-TGACCTN$_x$TGACCT-3' (SEQ ID NO: 9); wherein the element comprises at least one DR oriented in either a forward or reverse orientation as indicated by Z ("f"=forward, "r"=reverse); wherein Y equals 1 to 8 forward and/or reverse direct repeats; and X equals 1 to about 12. For example, the DR1f refers to "direct repeat 1-forward." This means that there is a single forward oriented DR sequence with two half-sites, with a single nucleotide space between the two half-sites. As such, DR1f has the sequence AGGTCANAGGTCA (SEQ ID NO: 10), wherein N is any base. The invention also envisages hormone response elements in various orientations. For example, 2DR1ff might represent AGGTCANAGGTCAAGGTCANAGGTCA (SEQ ID NO: 11; two adjacent DRs in the same orientation) and 2DR1fr AGGTCANAGGTCATGACCTNTGACCT (SEQ ID NO: 12; two adjacent DRs in the opposite orientation as the first example.) One of ordinary skill in the art could readily appreciate the potentially large number of variations and combinations envisaged. Preferably, the nuclear hormone receptor response element is a DR1, DR2, DR4, or DR12 response element with the proviso that envisaged receptor response element does not include a specific 4DR12fffr element with a reverse oriented DR12 preceded by three forward oriented DR12s.

An another embodiment, the nuclear hormone receptor response element comprises the hormone response element EcRE having the sequence 5; GAGGTCAATGACCTC-3' (SEQ ID NO: 7).

The term "core promoter region" refers to a DNA sequence that acts as a site of initiation for the formation of a transcriptional complex that will transcribe one or more nucleic acid sequences. It is located upstream with respect to the direction of transcription of the transcription initiation site of the gene, and is structurally identified by the presence of a binding site for DNA-dependent RNA polymerase and transcription initiation sites. Most preferably, the promoter is down stream of and operably linked to the nuclear hormone response element. More preferably, the promoter is the BJHSP1 core promoter, the JHE core promoter (SEQ ID NO: 22), BJHSP2Core (SEQ ID NO: 5), AJHSP1Core (SEQ ID NO: 3), BJHSP1 (SEQ ID NO: 4) or the ArylCore (SEQ ID NO: 6). These core promoter sequences are described in Jones et al., (1995) Gene, 173: 209-214.

The term "induction" refers to an increase in nucleic acid sequence transcription or expression brought about by nuclear hormone receptor response element binding of a ligand activated/homo- or heterodimerized nuclear hormone receptor relative to some basal level of transcription. Preferably, hetero- or homodimerized ligand bound nuclear hormone receptor binds to a nuclear hormone receptor response element and induces transcription of a reporter gene as measured by construct activity.

The term "construct activity" refers to the extent of expression of a nucleotide sequence that is operably linked to the nuclear hormone receptor response reporter construct whose activity is being measured. Construct activity may be measured directly by determining the amount of RNA transcript produced, for example by Northern blot analysis or indirectly by determining the amount of product coded for by the linked nucleic acid sequence, such as a reporter nucleic acid sequence linked to the promoter. Alternatively, construct activity is measured as a function of the activity of a protein encoded by a reporter nucleic acid sequence operably linked to the receptor response element and core promoter.

A "reporter nucleic acid sequence" is a DNA molecule that expresses a detectable gene product, which may be RNA or protein. The detection may be accomplished by any method known to one of skill in the art. For example, detection of mRNA expression may be accomplished by using Northern blot analysis and detection of protein may be accomplished by staining with antibodies specific to the protein, e.g. Western blot analysis. Preferred reporter nucleic acid sequences are those that are readily detectable. A reporter nucleic acid sequence may be operably linked in a DNA construct with a nuclear hormone receptor response element such that detection of the reporter nucleic acid sequence product provides a measure of the construct activity of the regulatory sequence. Examples of reporter nucleic acid sequences include, but are not limited to, those coding for alkaline phosphatase, chloramphenicol acetyl transferase (CAT), luciferase, beta-galactosidase and alkaline phosphatase.

Construction of expression vectors containing the novel nuclear hormone receptor response reporter constructs, can be accomplished by methods known to one of skill in the art. Typically nuclear hormone receptor response reporter construct will be cloned into an expression vector via suitable restriction endonuclease sites. The expression vector may be a plasmid, virus or a cosmid, for example. The cloned expression vector may then be transfected into the target host cells and successfully transformed cells may be selected based on the presence of a suitable marker nucleic acid sequence as described above.

DNA is commonly transferred or introduced into recipient mammal or insect cells by calcium phosphate-mediated gene transfer, electroporation, lipofection, viral infection and the like. General methods, vectors and general considerations for gene transfer and expression may be found in M. Kriegler, Gene Transfer and Expression: A Laboratory Manual, Stockton Press (1990). Direct gene transfer to cells in vivo is achieved by the use of modified viral vectors, including retroviruses, adenoviruses, adeno-associated viruses and herpes viruses, liposomes, and direct injection of DNA into certain cell types. See, e.g., Wilson, Nature, 365: 691-692 (1993); Plautz et al, Annals NY Acad. Sci., 716: 144-153 (1994); Farhood et al, Annals NY Acad. Sci., 716: 23-34 (1994) and Hyde et al Nature, 362: 250-255(1993). Furthermore, cells may be transformed ex vivo selected as described earlier and introduced directly at localized sites by injection, e.g., intra-articular, intracutaneous, intramuscular and the like.

This invention includes substantially identical polynucleotides that hybridize under stringent conditions (as defined herein) to all or a portion of the invention's mutant receptor sequences or hormone response element sequences (i.e., target sequences) or their complements. Under stringent hybridization conditions, only highly complementary, i.e., substantially similar nucleic acid sequences, hybridize. Preferably, such conditions prevent hybridization of nucleic acids having 4 or more mismatches out of 20 contiguous nucleotides, more preferably 2 or more mismatches out of 20 contiguous nucleotides, most preferably one or more mismatch out of 20 contiguous nucleotides. The hybridizing portion of the hybridizing nucleic acid is at least about 80%, preferably at least about 95%, or most preferably about at least 98%, identical to the sequence of a portion or all of a target sequence, or its complement.

Hybridization of a nucleic acid to a nucleic acid sample under stringent conditions is defined below. Nucleic acid duplex or hybrid stability is expressed as a melting temperature ($T_m$), which is the temperature at which the probe dissociates from the target DNA. This melting temperature is used to define the required stringency conditions. If sequences are to be identified that are substantially identical to the probe, rather than identical, then it is useful to first establish the lowest temperature at which only homologous hybridization occurs with a particular concentration of salt (e.g. SSC or SSPE). Then assuming that 1% mismatching results in a 1° C. decrease in $T_m$, the temperature of the final wash in the hybridization reaction is reduced accordingly (for example, if sequences having >95% identity with the probe are sought, the final wash temperature is decrease by 5° C.). In practice, the change in $T_m$ can be between 0.5° C. and 1.5° C. per 1% mismatch.

Stringent conditions involve hybridizing at 68° C. in 5×SSC/5× Denhart's solution/1.0% SDS, and washing in 0.2×SSC/0.1% SDS at room temperature. Moderately stringent conditions include washing in 3×SSC at 42° C. The parameters of salt concentration and temperature be varied to achieve optimal level of identity between the primer and the target nucleic acid. Additional guidance regarding such conditions is readily available in the art, for example, Sambrook, Fischer and Maniatis, Molecular Cloning, a laboratory manual, (2nd ed.), Cold Spring Harbor Laboratory Press, New York, (1989) and F. M. Ausubel et al eds., Current Protocols in Molecular Biology, John Wiley and Sons (1994).

The invention provides a set of biochemical and cellular tools and assays that enable the user to identify to chemical compounds that are effective in activating or blocking particular hormone-dependent regulatory pathways in various organisms.

The invention relates to mutant nuclear hormone receptors that encode mutant nuclear hormone receptors, in which particular amino acid residues are substituted with respect to wild type, so as to be able to detect ligand binding to the mutant receptor by either a change in a physical property of the mutant receptor and/or an transcriptional induction of a nuclear hormone receptor construct. These proteins bind and interact with ligands in substantially the same way as their wild type counter part. However, certain amino acid substitutions readily allow changes in protein fluorescence with respect to wild type facilitating the detection between ligand and receptor.

Another aspect of the invention relates to a method identifying ligands of nuclear hormone receptors comprising: contacting a mutant nuclear hormone receptor protein with a candidate ligand; and determining whether there is a change in a physical property of the protein or a change in the transcriptional activity of the protein. Preferably, such a method is scaled up and carried out by an apparatus capable of simultaneously screening libraries of small molecules generated by combinatorial chemistry or similar techniques typical in the art.

Another aspect of the invention relates to a nucleic acids that encode dominant negative mutant nuclear hormone receptors. Preferably, dominant negative mutants are used to interfere with endogenous nuclear hormone signaling pathways. Although the skilled artisan could envisage a multitude of uses, preferably, such mutants are used in combination with nuclear hormone receptor reporter construct to control that a candidate ligand is binding an endogenous nuclear hormone receptor and that this binding is the result of in induction of the nuclear hormone receptor reporter construct rather than some unforeseen independent mechanism.

Another aspect of the invention relates to a nuclear hormone receptor response element denoted by the formula YDRXZ comprising a direct repeat (DR) comprising two half sites separated by X nucleic acid bases; wherein Z indicates a forward DR sequence of 5'-AGGTCA(N)$_x$AG-GTCA-3' (SEQ ID NO: 8) and/or a reverse DR sequence of 5'-TGACCT(N)$_x$TGACCT-3' (SEQ ID NO: 9); wherein the element comprises at least one DR oriented in either a forward or reverse orientation; wherein Y equals 1 to 8 forward and/or reverse direct repeats; and X equals 1 to about 12. Such elements may be operably linked to a wide variety of core or basal promoters to test nuclear hormone receptor activation.

Another aspect of the invention relates to nuclear hormone receptor reporter construct comprising a nuclear hormone receptor response element, a promoter and a reporter nucleic acid sequence operably linked to one another; wherein the hormone receptor response element denoted by the formula YDRXZ comprises a direct repeat (DR) comprising two half sites separated by X nucleic acid bases; wherein Z connotes a forward DR sequence of 5'-AGGTCA (N)$_x$AGGTCA-3' (SEQ ID NO: 8) and/or a reverse DR sequence of 5'-TGACCT(N)$_x$TGACCT-3' (SEQ ID NO: 9); wherein the element comprises at least one DR oriented in either a forward or reverse orientation; wherein Y equals 1 to 8 forward and/or reverse direct repeats; and X equals 1 to about 12; and wherein the promoter is selected from the group consisting of SEQ NOs: 3, 4, 5, and 6.

In another aspect of the invention, the set of tools and assays disclosed herein are useful for screening for commercial compounds that will have particular effects on the function of USP/RXR receptors will lead to the identification of environmentally safe, new insecticides that are specific for disrupting the hormone receptor-dependent physiological regulation of insects (pests of food/fiber/ornamental plants, or vectors of disease agents) but not disrupt the hormone receptor-dependent physiological regulations of humans or other non-target vertebrates. These assays could be designed in a 'scaled up' format, in which thousands of test chemicals are effectively assays for particular effects to disrupt the hormone receptor-dependent regulation of insects.

EXAMPLE 1

Cell Culture and Transfections

Spodoptera frugiperda cell line, Sf9, was maintained and transfected as described previously Jones et al (1998) Biochem. J. 335, 79-84; Jones et al. (2000) Biochem. J. 346, 233-240. As an internal control to compare activities of different constructs, 0.3 µg of a constituitive heat-shock promoter-driven β-galactosidase gene was cotransfected. To study the role of USP in activation of the nuclear hormone receptor response element fused to core promoter in methyl epoxyfarnesoate-treated cells, cloned D. melangaster USP (dUSP) cDNA and its derivatives containing mutations in the ligand-binding pocket were cotransfected with the reporter and internal control plasmids. At 36 h after the transfection, the cells were treated with 75 µm methyl epoxyfarnesoate (Sigma) in ethanol carrier (1% final ethanol concentration) or just ethanol carrier only (previous studies demonstrated methyl epoxyfarnesoate effects were dose dependent, with maximum near 75 µm). After 48 h of the treatment, the cells were harvested and the activity of the luciferase reporter was measured using a luciferase assay kit (Promega) in a multipurpose scintillation counter (Beckman, Fullerton, Calif.). β-Galactosidase activity was measured using chlorophenol red-α-d-galactopyranoside monosodium (CPRG; Roche Molecular Biochemicals) as a colorimetric substrate.

EXAMPLE 2

Nuclear Hormone Receptor Response Elements

The sequences and characteristics of the core promoter (61 to +28) of the JHE gene were described by Jones et al. (2001) Insect Biochem. Mol. Biol. 32, 33-49; Jones et al (1998) Biochem. J. 335, 79-84; 79-84; Jones et al. (2000) Biochem. J. 346, 233-240. The core promoter responds to respond to methyl epoxyfarnesoate through a heterologous 5' flanking direct repeat motif in cell transfection assay. This Core promoter reporter was cloned into KpnI/BglII sites of pGL3. An NheI site was then placed immediately 5' to the KpnI site, and multiple direct repeat (DR) sequences were cloned into the NheI site by the following method. Complementary oligonucleotides encoding the particular DR motif were synthesized, with each oligonucleotide possessing at its 5' end a four base overhang of an NheI restriction site (CTAG). Upon annealing, the double stranded oligonucleotides would then have a CTAG overhang at each 5' end. The annealed oligonucleotides were then ligated into concatamers, fractionated by native PAGE and the gel fractions corresponding to higher concatamer forms recovered and ligated into the NheI site. Specific DR sequences for the oligonucleotides were (upper strand) for DR1: 5'-CAAGGTCAAAGGTCAG-3' (SEQ ID NO: 13), for DR4: 5'-CAAGGTCAAGAAAGGTCAG-3' (SEQ ID NO: 14), for DR12: 5'-CAAGGTCAAGAAGGCCAAAGAGGTCAG-3' (SEQ ID NO: 15; CTAG on 5' ends not shown). The recovered YDRXCore constructs (X representing 1, 4 or 12 intervening bases; Y representing the number of tandem pairs of direct repeats) were verified by sequencing. The intervening sequences in the DR1 and DR4 motifs were randomly chosen, while the DR12 sequence used is found in the ecdysteroid-sensitive ng-1 and ng-2 genes that are expressed during metamorphosis of D. melanogaster, and can serve in vitro as a binding site for the various receptor dimers involving USP (ecdysteroid receptor (EcR)/USP heterodimer, USP/DHR38 heterodimer and USP/USP homodimer.

Placement of four tandem copies of a DR12 motif (CAAGGTCANNNNNNNNNNNNAGGTCAG SEQ ID NO: 16), FIG. 1A) at 5' to the Core promoter reporter (4DR12Core construct, FIG. 1B) yielded a 10-fold induction in promoter activity in response to treatment of the transfected Sf9 cells with methyl epoxyfarnesoate (FIG. 1B). In contrast, insertion of a cassette containing four tandem copies of either a DR1 or DR4 motif yielded only a 2.5- and 3.5-fold induction, respectively (FIG. 1B). This differential result confirms that the 10-fold activation observed with the 4DR12Core construct was caused by the sequence of the inserted DR12 cassette itself, and was not due to either insertional disruption or creation of a putative cryptic regulatory element at the vector multiple cloning site. Due to the highest reporter activity being obtained with the DR12 motif, we focussed on the DR12 repeat construct, towards the goal of the study of ligand activation of USP.

We then confirmed that sequences in the AGGTCA half sites themselves of the DR12 motif were necessary for transducing the methyl epoxyfarnesoate signalling. We took advantage of the previous report that mutation of each half site abrogated the ability of DR12 motif to enhance ecdysteroid transcriptional activation D'Avino et al. (1995) Mol. Cell. Endo. 113, 1-9. When we mutated here each half site of the DR12 motif (in a construct containing a single DR12 in order to simplify mutational analysis; 1DR12mutCore), the responsiveness of the 1DR12mutCore to methyl epoxyfarnesoate was no greater than the background of a Core promoter with no enhancer (FIG. 2B); in contrast to the responsiveness of the Core promoter in the presence of a wild-type DR12 (1DR12Core, FIG. 2B).

EXAMPLE 3

Nuclear Extracts and Electrophoretic Mobility Shift Assay

Nuclear extracts were isolated from Sf9 cells as previously described Jones et al. (2001) Insect Biochem. Mol. Biol. 32, 33-49; Jones et al (1998) Biochem. J. 335, 79-84; 79-84; Jones et al. (2000) Biochem. J. 346, 233-240. For the DR12 probe, the double stranded DR12 oligonucleotide (sequence as shown above) was 5' end-labelled with $^{32}$P by T4 polynucleotide kinase (New England Biolabs Inc.), and then purified from a 20% native polyacrylamide gel. The same double stranded DR12 oligonucleotide was used in 100-fold excess as a self competitor. For the 4DR12Core probe, the 4DR12Core sequence was liberated from the vector as a 148-bp ClaI/HindIII fragment, and was 5' end-labelled with $^{32}$P and purified. The same, unlabelled fragment was used at 100-fold excess as a self competitor. As a negative control for specificity in gel shifts, the 36 bp BglII/KpnI polylinker region fragment of the pGL3 vector was liberated and recovered from low melting point agarose gels and used as a 100 nonself competitor (sequence: GGTACCGAGCTCTTACGCGTGCTAGC-CCGGGCTCGA, SEQ ID NO: 17). Either a final concentration of 500 nm of His-tagged wild-type USP or His-tagged mutant Cys472Ala/His475Leu (=C472A/H475L), or five micrograms of nuclear proteins, were incubated with the given probe on ice for 30 min in binding buffer (10 mM Tris/HCl, pH 7.5; 50 mM NaCl, 0.5 mM EDTA, 5% glycerol, 1 mM MgCl2, and 1 mM dithiothreitol). In some experiments, nuclear proteins were preincubated with the probe for 30 min followed by incubation with anti-USP mAb (a gift from F. Kafatos, EMBL, Heidelberg), or monoclonal Elav antibody (Developmental Studies Hybridoma Bank, University of Iowa), for an additional 1 h on ice. Samples were then subjected to 4% (w/v) polyacrylamide gel electrophoresis in 0.5 Tris/borate/EDTA buffer. After electrophoresis, the gels were dried and exposed to Kodak film at 70° C. for 12-48 h.

As an independent confirmation of the important role of the two direct repeat half sites in the DR12 motif, we demonstrated that in a gel mobility shift assay with Sf9 nuclear extracts, the DR12 motif probe yielded a shifted probe band that could be competed with excess, unlabelled wild-type DR12. However, the same DR12 mutated in its two half sites that had failed to support methyl epoxyfarnesoate-enhanced transcription in the cell transfection assay also correspondingly failed to compete with the wild-type DR12 probe in the gel shift assay (FIG. 2A), confirming the functional necessity of the two half sites for interaction with a nuclear component(s). Thus, the lack of binding to the mutant DR12 combined with the lack of a transcriptional effect of that same mutant DR12 indicates that the specific binding to the wild-type DR12 observed here relates to its positive action to transduce the methyl epoxyfarnesoate signalling observed in the transfection assay. The gel mobility shift assay using Sf9 nuclear extracts detected a single major complex binding to the DR12 probe (FIG. 2C). An anti-dUSP mAb (AB11, epitope on DNA binding domain) displaced the endogenous USP in the major complex binding to the DR12 probe (FIG. 2C). The specificity of the AB11 monoclonal antibody effect on USP binding was further confirmed in that no such effect was produced by a negative control monoclonal antibody against the transcription factor Elav.

EXAMPLE 4

USP Mutants

Point mutations in the ligand-binding domain of dUSP were made with a Chameleon™ double-stranded site-directed mutagenesis kit (Stratagene) according to the manufacturer's instructions. The selection primer used to change the unique NdeI (underlined) site in the pIE1-4 vector was CGGTATTTCACACCG CAcATGGTGCACTCTCAGTACAATC (SEQ ID NO: 18). The primer to mutate Q288 to alanine in the ligand-binding pocket was: GTGCCAAGTGGTCAACAAA gcGCTCTTCCAGATGGTCGAATAC (SEQ ID NO: 19). A primer that targeted two amino acids was used to make the double mutation in C473A and H476L because of their adjacent locations, with the sequence: GCGATCGAT-CAGCCTGAAGgcCCAGGAT CtCCTGTTCCTCTTCCGCATTAC (SEQ ID NO: 20). A primer that replaced two proline residues (P498, P499) at the end of α-helix 12 with tryptophan residues was: 5'-CTTTCTCGAGCAGCTGGAGGCGtgG tgGCCACCCGGCCTGGCGATGAAACT-3' (SEQ ID NO: 21). All mutant constructs were confirmed by DNA sequencing.

For expressing dUSP in Sf9 cells, PCR-generated full-length wild-type and point-mutated dUSP coding sequences were cloned into PmeI and NotI sites of the pIE1-4 vector (Novagen) and confirmed by sequencing, and for bacterial overexpression were cloned into pET32EK (Novagen).

EXAMPLE 5

Extraction of Total Proteins and Immunoblotting Analysis

Total Sf9 cell protein extracts from transfected Sf9 cells were fractionated by SDS/PAGE, 8% (w/v) polyacrylamide gel, and then transferred onto a nitrocellulose membrane. USP was detected using a primary USP AB11 monoclonal antibody and with an anti-mouse IgG-AP secondary Ig (Bio-Rad) by a BCIP/NBT color development solution (Bio-Rad). The USP signals were normalized by an internal control, β-actin, which was detected by a primary polyclonal β-actin antibody (Sigma) and with an anti-rabbit IgG-AP secondary Ig (Southern Biotechnology Associates, Inc.).

EXAMPLE 6

Purification of the His-USP Fusion Protein and Ligand-binding Assay

The homodimer-enriched fraction of bacterial recombinant His-dUSP fusion protein was purified by nickel resin selection, elution with imidazole, centrifugal concentration, and then gel permeation chromatography (Superdex 200) with procedures and chemical sources exactly as already described previously Jones et al. (2000) Insect Biochem. Mol. Biol. 30, 671-679. The homodimer-enriched fraction of the purified His-USP fusion protein was raised to 2 ml of NaCl and a final concentration of 0.5 µm. For a fluorescence-based ligand-binding assay based on intrinsic tryptophan fluorescence Jones et al. (2001) Insect Biochem. Mol. Biol. 32, 33-49; Jones et al (1998) Biochem. J. 335, 79-84; 79-84; Jones et al. (2000) Biochem. J. 346, 233-240; Jones et al (1997) Proc. Natl. Acad. Sci. USA 94, 13499-13503, ligand or ethanol carrier was added and the receptor preparation excited at 290 nm and monitored for emission at 340 nm, until the signal from the receptor had stabilized. Fluorescence was measured three times for each sample, with standard deviation typically smaller than the graphical plotted datum point. Each fluorescence experiment was replicated on three or more independent occasions, each time with similar results.

Figure 4A:
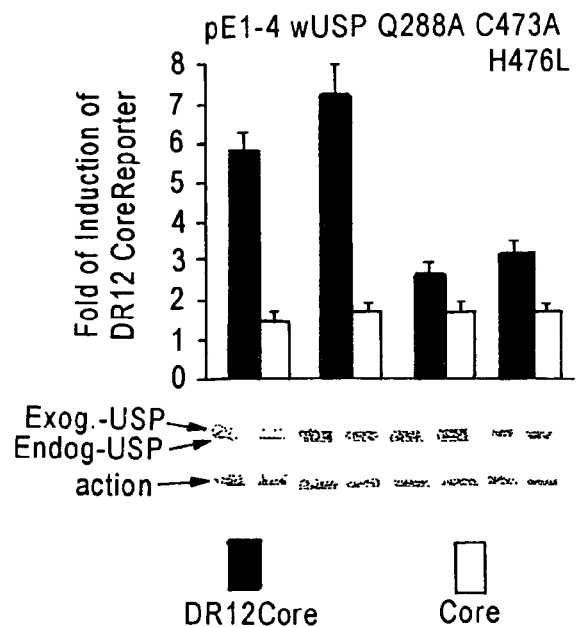
FIG. 4. Dominant negative activity of USP ligand-binding pocket mutants. (A) Histogram (shaded boxes) shows the dominant negative effect of transfected dUSP mutant and the double mutant (C472A/H475L) on methyl epoxyfarnesoate-activation of 4DR12Core reporter promoters, whereas transfected wild-type dUSP shows no such suppression of methyl epoxyfarnesoate activation, in comparison with transfection of Core reporter vector (reporter and expression plasmids transfected at 1:1 ratio). Transfection of neither the wild-type USP nor either mutant had any effect on the minimal basal activation of the Core promoter in the absence of the DR12 motif (clear boxes). Immunoblot of transfected cellular extracts with anti-(α-actin) and anti-dUSP (AB11) mAbs verified that the overexpression of mutant and wild-type dUSP did not affect the level of expression of endogenous USP, and that the transfected mutant and transfected wild-type dUSP were expressed at similar levels to each other. The molecular weights of the transfected and endogenous USPs detected by immunoblotting were about equal to 50 and 52 kDa, respectively, as estimated by molecular size standards run in parallel lanes (not shown). (B) Progressive increase in ratio of transfected dominant negative plasmid DNA relative to 4DR12Core reporter plasmid DNA yielded an increasing dominant negative suppression of methyl epoxyfarnesoate activation of reporter plasmid. Immunoblot verifies that the progressively higher overexpression of the mutant dUSP (C472A/H475L) did not affect the level of expression of endogenous USP. Inset above shows calculation of transcriptional activation ratio of reporter promoter activity in methyl epoxyfarnesoate-treated cells relative to EtOH treated cells, as a function of the ratio of the amount of transfected mutant dUSP plasmid relative to amount of transfected reporter plasmid. (C) Transfection of plasmid expressing wild-type USP rescues the dominant negative-suppression of methyl epoxyfarnesoate-activation of the reporter promoter. Open circle, methyl epoxyfarnesoate activation of 4DR12Core in the absence of USP expressing plasmid. Hashed circle, methyl epoxyfarnesoate activation is suppressed by transfection with the C472A/H475L dominant negative mutant. Filled circles, methyl epoxyfarnesoate activation is progressively restored by increasing doses of plasmid expressing wild-type dUSP. In A-C, hormone-treated cells received 75 μm of methyl epoxyfarnesoate.

His-tagged dUSP dominant negative double mutant Cys472Ala/His475Leu (C472A/H475L) was over expressed in methyl epoxyfarnesoate-treated Sf9 cells that were cotransfected with the 4DR12Core reporter plasmid. Cells transfected with either empty pIE1-4 vector, or that vector expressing wild-type dUSP, responded to methyl epoxyfarnesoate application with a similar induction of the 4DR12Core promoter (FIG. 4A). However, cells transfected with the plasmid expressing the C472A/H475L mutant exhibited a distinct suppression in the level of methyl epoxyfarnesoate-induced activation, as compared with the activation observed for cells transfected with either the empty plasmid or plasmid expressing wild-type dUSP (FIG. 4A). In addition, cotransfection of the empty vector, or vector expressing either wild-type dUSP or the C472A/

H475L mutant, did not affect the basal activation exhibited when the Core promoter without DR12 motifs was used. Together, these data demonstrate that the suppression in methyl epoxyfarnesoate-induced activation caused by overexpression of the C472A/H475L double mutant was not due to nonspecific titration of coactivators required by a receptor other than USP and not due to disruption of Core-binding basal transcription components independent of action through the DR12 enhancer. In addition, overexpression of either the C472A/H475L double mutant or the wild-type dUSP did not change the level of endogenous USP (FIG. 4A), confirming that overexpression of exogenous dUSP did not indirectly affect the methyl epoxyfarnesoate-activation pathway by disruption of endogenous USP expression.

Figure 4B:
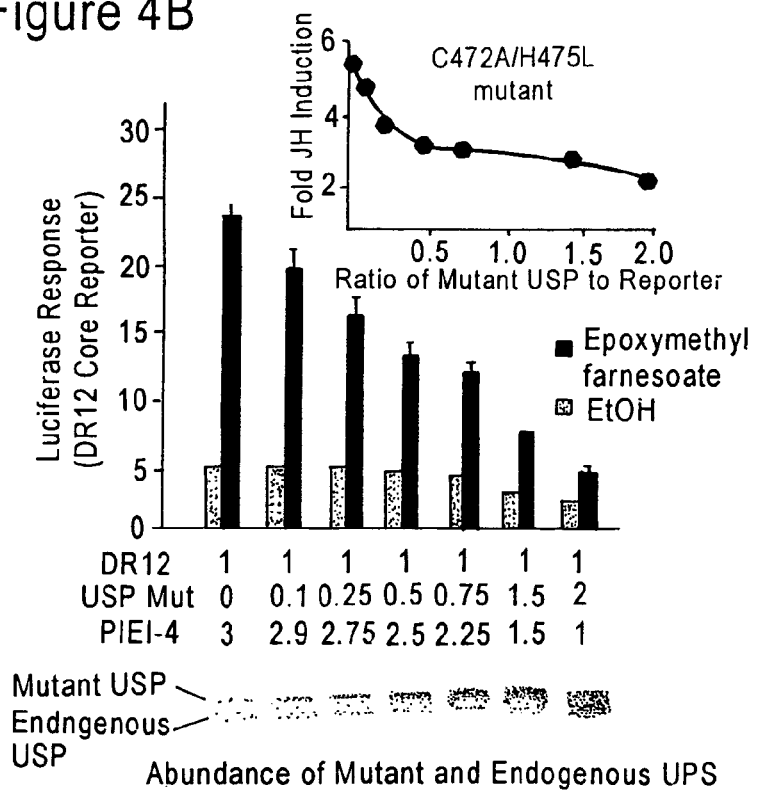
Figure 4C:
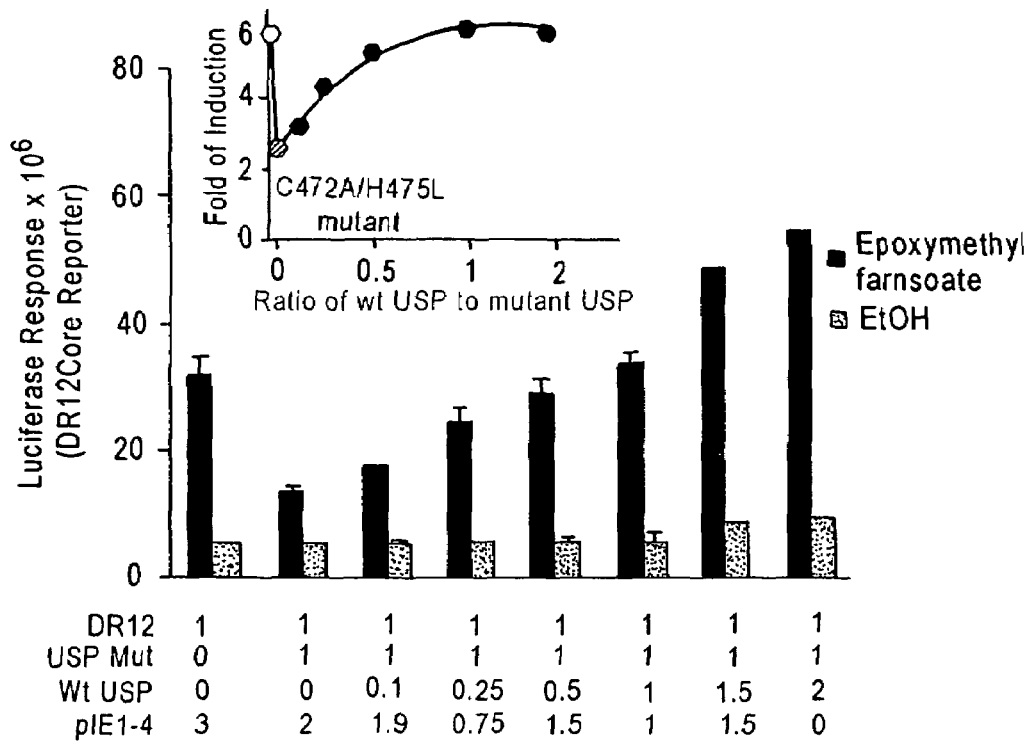

Under the model that overexpression of the C472A/H475L double mutant competed with endogenous USP in the pathways for transduction of the exogenous methyl epoxyfarnesoate signal, the level of effect of the double mutant ought to be dependent on its dose. Indeed, a progressive increase in the intracellular concentration of this double mutant (with endogenous USP level remaining unchanged) caused progressive suppression in the methyl epoxyfarnesoate-activation of the DR12Core promoter, down to the transcriptional level observed for the Core promoter without DR12 enhancers (FIG. 4B). Over the range of the progressive suppression of the methyl epoxyfarnesoate-activated transcription there was no effect of the double mutant on the basal level of transcription in EtOH-treated controls. This background of the blocked activation pathway was used to test whether activation by methyl epoxyfarnesoate treatment was actually dependent on the presence of wild-type USP. As shown in FIG. 4C, the activation of the 4DR12Core promoter in methyl epoxyfarnesoate-treated cells was monotonically restored in a manner dependent on the increasing dose of the added wild-type dUSP. Again, over the range of the monotonic restoration of methyl epoxyfarnesoate-activated transcription, there was no effect of the transfected wild-type dUSP on the basal level of transcription in EtOH-treated controls.

Figure 5A:
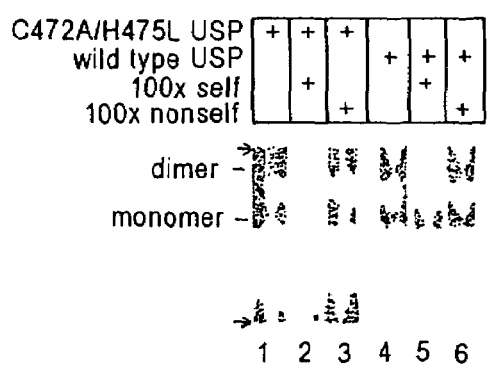
FIG. 5. Bacterially overexpressed double mutant dUSP (C472A/H475L) and wild-type dUSP analyzed for binding to DNA or to ligand. (A) The wild-type dUSP and the C472AH475L mutant both similarly bound in part as a homodimer (upper band) and in part as a monomer (lower band) to a 4DR12 motif probe (identification of monomer and homodimer bands was made by comparative analysis of binding by other dimer-enriched vs. monomer-enriched fractions obtained from Superdex 200 chromatography, not shown). Control competitions with self and nonself unlabelled excess probes confirmed the specificity of binding. The similar formation of the homodimer form by the wild-type USP and mutant USP, along with the similar binding to DNA of the wild-type USP and mutant USP, confirm that the mutation to the ligand-binding pocket in C475A/H475L did not generally disrupt the structure of the receptor. (B) The homodimer-enriched fraction of each receptor preparation was then analyzed for binding to 75 μm methyl epoxyfarnesoate, using an intrinsic fluorescence assay method that tracks ligand binding (by suppression in receptor fluorescence) Jones et al., (2000) Insect Biochem. Mol. Biol. 30, 671-679; Jones et al. (2001), Insect Biochem. Mol. Biol. 32, 33-49. The wild-type dUSP exhibited binding to methyl epoxyfarnesoate in this assay. However, the double mutant dUSP exhibited no binding activity. Arrows show time of addition of methyl epoxyfarnesoate or EtOH carrier.

The ability of the C472A/H475L mutant to bind DNA and to homodimerize to confirm was examined that the mutations to the ligand-binding pocket did not generally deform receptor structure. As shown in FIG. 5A, under electrophoretic mobility shift assay conditions, both the wild-type dUSP and the C472A/H475L mutant dUSP similarly bound to a DR12 motif. In addition, both receptor preparations bound to the probe similarly in part as monomer and in part as homodimer. The homodimerization of RXR and other steroid receptor superfamily members is primarily due to contacts in the ligand-binding domain that are outside of the ligand-binding pocket (in addition to some contacts also in the DNA-binding domain). The similar DNA binding and homodimerization capacities of the wild-type dUSP and mutant C472A/H475L dUSP is strongly indicative that the DNA-binding domain, and the parts of the ligand-binding domain that are outside of the ligand-binding pocket, are in a functionally similar conformation for both the wild-type and mutant receptors. Thus, any difference detected in ligand binding of the two receptors is most reasonably inferred as arising from differences in the architecture inside the cavity of the ligand-binding pocket due to the C472A/H475L point mutations.

EXAMPLE 7

Figure 5B:
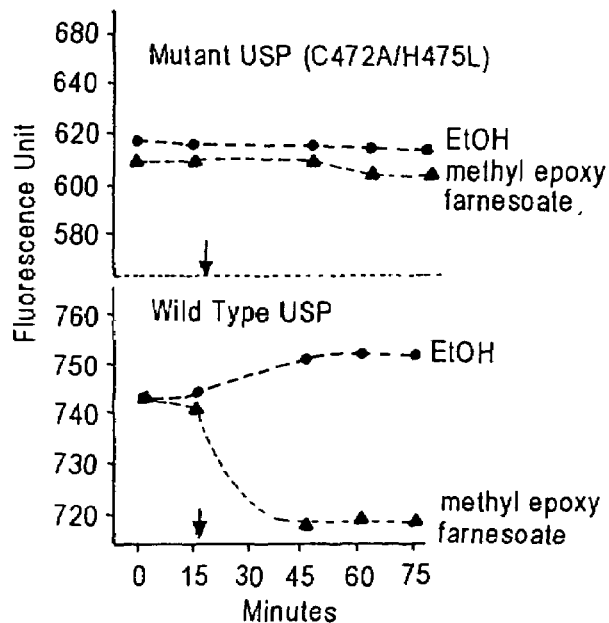

The ability of the wild-type dUSP and dominant negative, ligand-binding pocket mutant dUSP to bind methyl epoxyfarnesoate was tested. In a ligand-binding assay that detects methyl epoxyfarnesoate binding through its effects to suppress intrinsic fluorescence of dUSP, Jones et al., (1998) Biochem. J. 335, 79-84., Jones et al. (1997) Proc. Natl. Acad. Sci. USA 94, 13499-13503, the bacterially overexpressed His-tagged wild-type dUSP indeed exhibited suppressed the fluorescence due to the binding of methyl epoxyfarnesoate (FIG. 5B). However, the C472A/H475L mutant dUSP did not exhibit a significant response to epoxymethyl farnsoate (FIG. 5B). This result was reproduced with independent preparations of the wild-type dUSP and C472/H475L dUSP. These results indicate that C472A/H475L behaves as a dominant negative mutant in the pathway for methyl epoxyfarnesoate activation of the 4DR12Core promoter and that the activity is due to the effect of the C472A/H475L mutations on the ligand-binding activity of USP.

EXAMPLE 8

USP Mutants with Altered Fluorescence

Figure 6A:
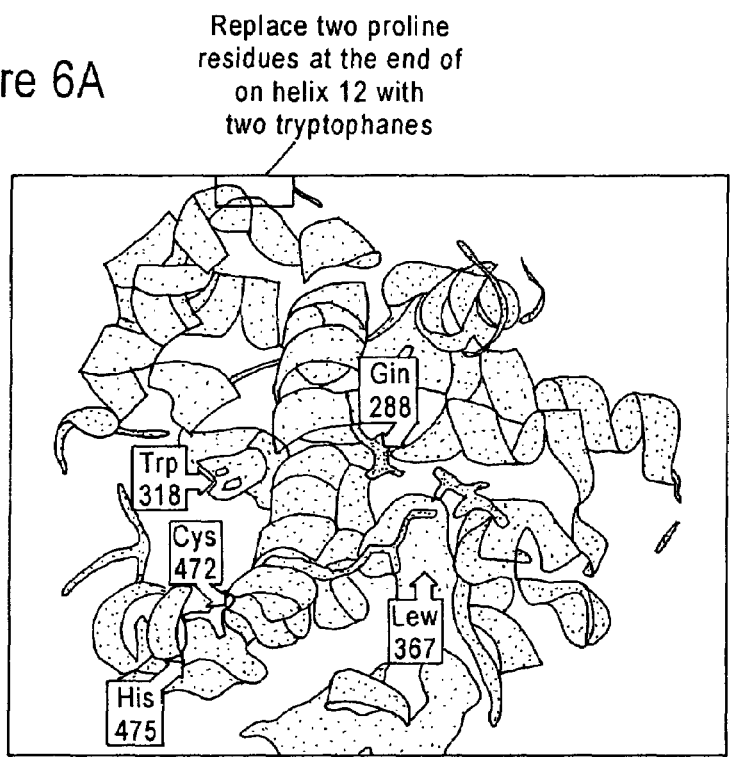
FIG. 6. Fluorescence response of wild-type and P498W/P499W mutant USP to farnesoid ligands. (A) The location of the mutational placement of the two tryptophan residues at the end of α-helix 12. USP also possesses two natural tryptophan residues on helix 5 (W318, shown extending into pocket; W328, not shown, extending out of pocket). (B) Methyl epoxyfarnesoate binding to wild-type USP results in suppression of receptor fluorescence, while farnesol and ethanol carrier do not have that effect. (C) Methyl epoxyfarnesoate binding to P498W/P499W mutant results in a very different pattern of fluorescence response than wild-type USP in B, evidencing that α-helix 12 moves in its relative location upon USP binding of methyl epoxyfarnesoate. The wild-type USP and P498W/P499W similarly bound in part as monomer and in part as dimer to a DR12 probe in gel shift assay, evidencing that the P498W/P499W mutations did not affect receptor structure globally (not shown).
Figure 6B:
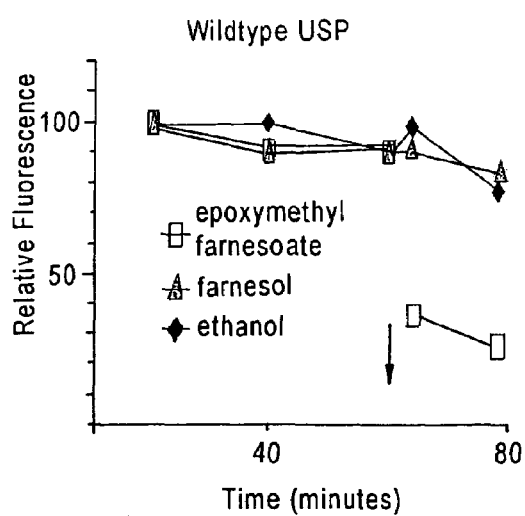
Figure 6C:
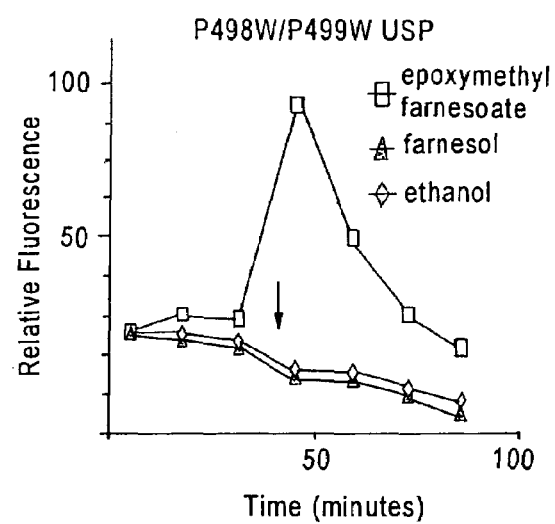

Some models of nuclear hormone receptor action postulate that binding of ligand to the ligand-binding pocket induces a tertiary conformational change involving the movement of α-helix 12 to a new position, Steinmetz et al (2001) Annu. Rev. Biophys. Biomol. Struct. 30, 329-359. However, the two published crystal structures of USP in complex with a phospholipid located at the opening of the ligand-binding pocket show α-helix 12 in a position that the investigators described as so firmly 'locked' against other residues of the ligand-binding domain that α-helix 12 would not be able to move even if the phospholipid were not present Billas et al. (2000) J. Biol. Chem. 276, 7465-7474; Jones et al (1997) Proc. Natl. Acad. Sci. USA 94, 13499-13503. Therefore, the hypothesis that α-helix 12 is so firmly locked in position that it does not move, by replacing two of the four continuous proline residues at the end of α-helix 12 with tryptophan residues, was tested. Under the model that USP α-helix 12 does not move upon binding of methyl epoxyfarnesoate in the ligand-binding pocket, these two tryptophan residues would only raise the constant background intrinsic fluorescence of the receptor, but, on account of the fact that they (as part of the fixed α-helix 12) do not move in position, their level of fluorescence would not change upon binding of methyl epoxyfarnesoate into the pocket. Therefore, their constant background fluorescence would not enhance or disguise the suppression in fluorescence exhibited by the two other natural tryptophan residues (on α-helix 5) upon binding of methyl epoxyfarnesoate. Alternatively, if α-helix 12 does move in position upon binding of methyl epoxyfarnesoate, then the change in the local environment of the two added tryptophan residues on α-helix 12 may change their fluorescence in a way that yields a markedly different overall fluorescence pattern for the receptor. Indeed, as FIG. 6B shows, in this test the wild-type USP with only two natural tryptophan resides on α-helix 5 exhibits a distinct suppression in fluorescence upon binding of methyl epoxyfarnesoate. In contrast, the mutant USP containing two additional tryptophan residues at the end of -helix 12 showed a much different profile, instead sharply increasing in fluorescence before then decreasing (Panel C). Collectively, these markedly different patterns of fluorescent response are most easily explained by a model in which -helix 12 does move in relative position, upon the binding of methyl epoxyfarnesoate into the ligand-binding pocket of USP.

EXAMPLE 9

Modelling of hRXR and *D. melanogaster* USP

Tertiary conformation of human RXR and *D. melanogaster* USP was analyzed by RASMOL software, using the coordinates reported into the Protein Data Bank by Bourguet and Moras (deposition number 1LB) and by Schwabe and Clayton (deposition number 1 HG4), respectively. Using a minimum energy conformation of farnesol as a scaffold, a conformation of epoxyfarnesoic acid was prepared and placed by hand into the ligand-binding pocket of USP along a generally similar trace as was reported for the (more bent) 9-cis retinoic acid ligand when the latter was cocrystalized with hRXR (Egea et al. EMBO J. 19, 2592-2601.)

Concerning the proximal end of the hRXR ligand, cocrystals of 9-cis RA and hRXR have also established that a glutamine residue on α-helix 3 (Gln275) makes contact with both the carbonyl carbon and a carboxylate oxygen (FIGS. 3A,B and 5). This glutamine residue is conserved in all reported USPs (FIG. 5C; Jones et al. (2000) Insect Biochem. Mol. Biol. 30, 671-679. Therefore, we mutated this Gln288 in dUSP to alanine (Gln288A), and found that this mutant dUSP also acted as a dominant negative suppressor of activation of the DR12Core reporter promoter in methyl epoxyfarnesoate-treated Sf9 cells (FIG. 4A).

In this disclosure there is described only the preferred embodiments of the invention and but a few examples of its versatility. It is to be understood that the invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances and procedures described herein. Such equivalents are considered to be within the scope of this invention.

What is claimed is:

1. An isolated nucleic acid having at least about 95% sequence identity over the complete length of the nucleic acid with SEQ ID NO: 1 or the complement thereof, wherein said nucleic acid or said complement thereof encodes a protein having a tryptophan residue in a first position corresponding to position 477 of SEQ ID NO: 2 and a tryptophan residue in a second position corresponding to position 479 of SEQ ID NO: 2, which upon binding an epoxy farnesoid-like ligand results in transcriptional activation of a nuclear hormone receptor reporter construct.

2. An isolated nucleic acid having at least about 95% sequence identity over the comnlete length of the nucleic acid with SEQ ID NO: 1 or the complement thereof, wherein said nucleic acid or said complement thereof encodes a protein having a tryptophan residue in a first position corresponding to position 477 of SEQ ID NO: 2, which upon binding an epoxy farnesoid-like ligand results in transcriptional activation of a nuclear hormone receptor reporter construct.

3. An isolated nucleic having at least about 95% sequence identity over the complete length of the nucleic acid with SEQ ID NO: 1 or the complement thereof, wherein said nucleic acid or said complement thereof encodes a protein having a tryptophan residue in a first position corresponding to position 479 of SEQ ID NO: 2, which upon binding an epoxy farnesoid-like ligand results in transcriptional activation of a nuclear hormone receptor reporter construct.

4. An isolated nucleic acid having at least about 95% sequence identity over the complete length of the nucleic acid with SEQ ID NO: 1 or the complement thereof, wherein said nucleic acid or said complement thereof encodes a protein having a tryptophan residue in a first position corresponding to position 302 of SEQ ID NO: 2, which upon binding an epoxy farnesoid-like ligand results in transcriptional activation of a nuclear hormone receptor reporter construct.

5. An isolated nucleic acid having at least about 95% sequence identity over the complete length of the nucleic acid with SEQ ID NO: 1 or the complement thereof, wherein said nucleic acid or said complement thereof encodes a protein having a tryptophan residue in a first position corresponding to position 315 of SEQ ID NO: 2, which upon binding an epoxy farnesoid-like ligand results in transcriptional activation of a nuclear hormone receptor reporter construct.

6. An isolated nucleic acid having at least about 95% sequence identity over the complete length of the nucleic acid with SEQ ID NO: 1 or the complement thereof, wherein said nucleic acid or said complement thereof encodes a protein having a phenylalanine residue in a first position corresponding to position 318 of SEQ ID NO: 2, which upon binding an epoxy farnesoid-like ligand results in altered fluoresecence with respect to the wild type *Drosophila melanogaster* protein Ultraspiracle.

7. An isolated nucleic acid having at least about 95% sequence identity over the complete length of the nucleic acid with SEQ ID NO: 1 or the complement thereof, wherein said nucleic acid or said complement thereof encodes a protein having a phenylalanine residue in a first position corresponding to position 328 of SEQ ID NO: 2, which upon binding an epoxy farnesoid-like ligand results in altered fluoresecence with respect to the wild type *Drosophila melanogaster* protein Ultraspiracle.

8. An isolated nucleic acid having at least about 95% sequence identity over the complete length of the nucleic acid with SEQ ID NO: 1 or the complement thereof, wherein said nucleic acid or said complement thereof encodes a protein having a phenylalanine residue in a first position corresponding to position 318 of SEQ ID NO: 2, and a phenylalanine residue in a second position corresponding to position 328 of SEQ ID NO: 2, which upon binding an epoxy farnesoid-like ligand results in altered fluoresecence with respect to the wild type *Drosophila melanogasier* protein Ultraspiracle.

9. An isolated nucleic acid having at least about 95% sequence identity over the complete length of the nucleic acid with SEQ ID NO: 1 or the complement thereof, wherein said nucleic acid or said complement thereof encodes a protein having an tryptophan residue in a first position corresponding to position 498 of SEQ ID NO: 2, a tryptophan residue in a second position corresponding to position 499 of SEQ ID NO: 2, and phenylalanine residue in a third position corresponding to position 318 of SEQ ID NO: 2, which upon binding an epoxy farnesoid-like ligand results in altered fluoresecence with respect to the wild type *Drosophila melanogaster* protein Ultraspiracle.

10. An isolated nucleic acid having at least about 95% sequence identity over the complete length of the nucleic acid with SEQ ID NO: 1 or the complement thereof, wherein said nucleic acid or said complement thereof encodes a protein having an tryptophan residue in a first position corresponding to position 498 of SEQ ID NO: 2, a tryptophan residue in a second position corresponding to position 499 of SEQ ID NO: 2, and phenylalanine residue in a third position corresponding to position 328 of SEQ ID NO: 2, which upon binding an epoxy farnesoid-like ligand results in transcriptional activation of a nuclear hormone receptor reporter construct.

11. An isolated nucleic acid having at least about 95% sequence identity over the complete length of the nucleic acid with SEQ ID NO: 1 or the complement thereof, wherein said nucleic acid or said complement thereof encodes a protein having an tryptophan residue in a first position corresponding to position 498 of SEQ ID NO: 2, a tryptophan residue in a second position corresponding to position 499 of SEQ ID NO: 2, and phenylalanine residue in a third position corresponding to position 318 of SEQ ID NO: 2, and phenylalanine residue in a fourth position corresponding to position 328 of SEQ ID NO: 2, which upon binding an epoxy farnesoid-like ligand results in altered fluoresecence with respect to the wild type *Drosophila melanogaster* protein Ultraspiracle.

12. An isolated nucleic acid having at least about 95% sequence identity over the complete length of the nucleic acid with SEQ ID NO: 1 or the complement thereof, wherein said nucleic acid or said complement thereof encodes a protein having an alanine residue in a first position corresponding to position 472 of SEQ ID NO: 2 and leucine residue in a second position corresponding to position 475 of SEQ ID NO: 2, which has dominant negative nuclear hormone receptor activity.

13. An isolated nucleic acid having at least about 95% seauence identity over the complete length of the nucleic acid with SEQ ID NO: 1 or the complement thereof, wherein said nucleic acid or said complement thereof encodes a protein having an arginine residue in a first position corresponding to position 302 of SEQ ID NO: 2, which has dominant negative nuclear hormone receptor activity.

14. An isolated nucleic acid having at least about 95% sequence identity with SEQ ID NO: 1 or the complement thereof, wherein said nucleic acid or said complement thereof encodes a protein having an arginine residue in a first position corresponding to position 293 of SEQ ID NO: 2, which has dominant negative nuclear hormone receptor activity.

15. An isolated nucleic acid having at least about 95% sequence identity over the complete length of the nucleic acid with SEQ ID NO: 1 or the complement thereof, wherein said nucleic acid or said complement thereof encodes a protein having an alanine residue in a first position corresponding to position 288 of SEQ ID NO: 2, which has dominant negative nuclear hormone receptor activity.

16. An isolated nucleic acid having at least about 95% sequence identity over the complete length of the nucleic acid with SEQ ID NO: 1 or the complement thereof, wherein said nucleic acid or said complement thereof encodes a protein having an alanine residue in a first position corresponding to position 366 of SEQ ID NO: 2, which has dominant negative nuclear hormone receptor activity.

17. An isolated nucleic acid having at least about 95% sequence identity over the complete length of the nucleic acid with SEQ ID NO: 1 or the complement thereof, wherein said nucleic acid or said complement thereof encodes a protein having an alanine residue in a first position corresponding to position 366 of SEQ ID NO: 2 and an alanine residue in a second position corresponding to position 288 of SEQ ID NO: 2 which has dominant negative nuclear hormone receptor activity.

18. A protein encoded by the isolated nucleic acid or complement thereof of any one of claims 1 to 11.

19. An isolated nucleic acid having at least about 95% sequence identity over the complete length of the nucleic acid with SEQ ID NO: 1 or the complement thereof, wherein said nucleic acid or said complement thereof encodes a protein having an arginine residue in a first position corresponding to position 314 of SEQ ID NO: 2 and which has dominant negative nuclear hormone receptor activity.

20. A protein encoded by the isolated nucleic acid or complement thereof of any one of claims 12 to 17 and 19.

* * * * *